US008298238B2

(12) United States Patent
Haines

(10) Patent No.: US 8,298,238 B2
(45) Date of Patent: Oct. 30, 2012

(54) METHODS AND APPARATUS FOR PIVOTABLE GUIDE SURFACES FOR ARTHROPLASTY

(75) Inventor: Timothy G. Haines, Seattle, WA (US)

(73) Assignee: Hudson Surgical Design, Inc., Seattle, WA (US)

( * ) Notice: Subject to any disclaimer, the term of this patent is extended or adjusted under 35 U.S.C. 154(b) by 930 days.

(21) Appl. No.: 12/187,210

(22) Filed: Aug. 6, 2008

(65) Prior Publication Data

US 2009/0138018 A1      May 28, 2009

Related U.S. Application Data

(63) Continuation of application No. 11/074,599, filed on Mar. 8, 2005, now abandoned, and a continuation of application No. 11/036,584, filed on Jan. 14, 2005, now Pat. No. 7,815,645, and a continuation of application No. 11/049,634, filed on Feb. 2, 2005, now abandoned.

(60) Provisional application No. 60/551,080, filed on Mar. 8, 2004, provisional application No. 60/551,078, filed on Mar. 8, 2004, provisional application No. 60/551,096, filed on Mar. 8, 2004, provisional application No. 60/551,631, filed on Mar. 8, 2004, provisional application No. 60/551,307, filed on Mar. 8, 2004, provisional application No. 60/551,262, filed on Mar. 8, 2004, provisional application No. 60/551,160, filed on Mar. 8, 2004, provisional application No. 60/356,320, filed on Jan. 14, 2004, provisional application No. 60/540,992, filed on Feb. 2, 2004.

(51) Int. Cl.
*A61F 5/00* (2006.01)

(52) U.S. Cl. ........................................... 606/87

(58) Field of Classification Search ................ 606/87, 606/88, 82, 83, 64, 79, 80, 84, 85, 86 R
See application file for complete search history.

(56) References Cited

U.S. PATENT DOCUMENTS 3,739,662 A      6/1973   Windelman et al.
(Continued)

FOREIGN PATENT DOCUMENTS

EP            0104732            4/1984
(Continued)

OTHER PUBLICATIONS

T.D.V. Cooke et al., *Universal Bone Cutting Device for Precision Knee Replacement Arthroplasty and Osteotomy*, 7 J. Biomed. Eng'g 45, 47, col. 2, ll. 52-57 (1985).

(Continued)

*Primary Examiner* — Eduardo C Robert
*Assistant Examiner* — James Palmer
(74) *Attorney, Agent, or Firm* — Patterson Thuente Christensen Pedersen, P.A.

(57) ABSTRACT

Cutting guides, cutting tools, and soft tissue management techniques permit the use of pivoting guide surfaces to facilitate in controlling the sweep or arc of a cutting tool used in connection with resection and arthroplasty procedures. In accordance with one embodiment, a guide structure is provided with one or more guide pivot aperture(s) and one or more guide pivot reference surface(s) that mate with a bushing assembly controlling a cutting tool. The bushing assembly possesses a bushing reference plan which mates with the pivot reference surface(s) of the guide structure and a bushing pivot pin which mates with the guide pivot aperture(s) of the guide structure. In one embodiment, a bushing guide lumen is operably coupled to the guide structure for articulated and/or axial guidance of the cutting tool.

14 Claims, 19 Drawing Sheets

U.S. PATENT DOCUMENTS

| | | |
|---|---|---|
| 3,748,662 A | 7/1973 | Helfet |
| 3,774,244 A | 11/1973 | Walker |
| 3,798,679 A | 3/1974 | Ewald |
| 3,816,855 A | 6/1974 | Saleh |
| 3,906,550 A | 9/1975 | Rostoker |
| 3,943,934 A | 3/1976 | Bent |
| 3,953,899 A | 5/1976 | Charnley |
| 3,958,278 A | 5/1976 | Lee |
| 3,977,289 A | 8/1976 | Tuke |
| 4,016,606 A | 4/1977 | Murray |
| 4,069,824 A | 1/1978 | Weinstock |
| 4,178,641 A | 12/1979 | Grundel |
| 4,207,627 A | 6/1980 | Cloutier |
| 4,213,209 A | 7/1980 | Insall |
| 4,249,270 A | 2/1981 | Bahler |
| 4,340,978 A | 7/1982 | Buechel |
| 4,349,058 A | 9/1982 | Comparetto |
| 4,353,135 A | 10/1982 | Forte |
| 4,358,859 A | 11/1982 | Schurman et al. |
| 4,421,112 A | 12/1983 | Mains |
| 4,457,307 A | 7/1984 | Stillwell |
| 4,474,177 A | 10/1984 | Whiteside |
| 4,479,271 A | 10/1984 | Bolesky |
| 4,487,203 A | 12/1984 | Androphy |
| 4,501,266 A | 2/1985 | McDaniel |
| 4,502,483 A | 3/1985 | Lacey |
| 4,524,766 A | 6/1985 | Petersen |
| 4,566,448 A | 1/1986 | Rohr, Jr. |
| 4,567,886 A | 2/1986 | Peterson |
| 4,568,348 A | 2/1986 | Johnson et al. |
| 4,584,999 A | 4/1986 | Arnegger |
| 4,586,496 A | 5/1986 | Keller |
| 4,586,933 A | 5/1986 | Shoji et al. |
| 4,653,488 A | 3/1987 | Kenna |
| 4,659,331 A | 4/1987 | Matthews |
| 4,662,889 A | 5/1987 | Zichner |
| 4,693,721 A | 9/1987 | Ducheyne |
| 4,703,751 A | 11/1987 | Pohl |
| 4,709,699 A | 12/1987 | Michael |
| 4,711,639 A | 12/1987 | Grundei |
| 4,714,472 A | 12/1987 | Averill |
| 4,714,473 A | 12/1987 | Bloebaum |
| 4,718,413 A | 1/1988 | Johnson |
| 4,721,104 A | 1/1988 | Kaufman |
| 4,722,330 A | 2/1988 | Russell |
| 4,731,086 A | 3/1988 | Whiteside |
| 4,736,086 A | 4/1988 | Obara |
| 4,736,737 A | 4/1988 | Fargie |
| 4,738,256 A | 4/1988 | Freeman |
| 4,759,350 A | 7/1988 | Dunn |
| 4,770,663 A | 9/1988 | Hanslik |
| 4,787,383 A | 11/1988 | Kenna |
| 4,822,365 A | 4/1989 | Walker |
| 4,834,758 A | 5/1989 | Lane |
| 4,841,975 A | 6/1989 | Woolson |
| 4,880,429 A | 11/1989 | Stone |
| 4,892,093 A | 1/1990 | Zarnowski |
| 4,893,619 A | 1/1990 | Dale |
| 4,896,663 A | 1/1990 | Vandewalle |
| 4,919,667 A | 4/1990 | Richmond |
| 4,926,847 A | 5/1990 | Luckman |
| 4,935,023 A | 6/1990 | Whiteside |
| 4,936,853 A | 6/1990 | Fabian |
| 4,938,762 A | 7/1990 | Wehrli |
| 4,938,769 A | 7/1990 | Shaw |
| 4,944,757 A | 7/1990 | Martinez |
| 4,950,298 A | 8/1990 | Gustilo |
| 4,952,213 A | 8/1990 | Bowman |
| 4,963,152 A | 10/1990 | Hofmann |
| 4,963,153 A | 10/1990 | Noesberger |
| 4,971,075 A | 11/1990 | Lee |
| 4,979,949 A | 12/1990 | Matsen |
| 5,002,545 A | 3/1991 | Whiteside |
| 5,002,547 A | 3/1991 | Poggie |
| 5,007,933 A | 4/1991 | Sidebotham |
| 5,007,934 A | 4/1991 | Stone |
| 5,021,056 A | 6/1991 | Hofman |
| 5,021,061 A | 6/1991 | Wevers |
| 5,032,134 A | 7/1991 | Lindwer |
| 5,041,138 A | 8/1991 | Vacanti |
| 5,047,032 A | 9/1991 | Jellicoe |
| 5,049,149 A | 9/1991 | Schmidt |
| 5,053,037 A | 10/1991 | Lackey |
| 5,059,037 A | 10/1991 | Albert |
| 5,062,852 A | 11/1991 | Dorr |
| 5,080,675 A | 1/1992 | Lawes |
| 5,092,869 A | 3/1992 | Waldron |
| 5,098,436 A | 3/1992 | Ferrante |
| 5,100,409 A | 3/1992 | Coates |
| 5,112,336 A | 5/1992 | Krevolin |
| 5,116,375 A | 5/1992 | Hofmann |
| 5,122,144 A | 6/1992 | Bert |
| 5,129,907 A * | 7/1992 | Heldreth et al. ................ 606/80 |
| 5,129,909 A | 7/1992 | Sutherland |
| 5,133,758 A | 7/1992 | Hollister |
| 5,133,759 A | 7/1992 | Turner |
| 5,137,536 A | 8/1992 | Koshino |
| 5,147,364 A * | 9/1992 | Comparetto ................... 606/85 |
| 5,147,365 A | 9/1992 | Whitlock |
| 5,147,405 A | 9/1992 | Van Zile |
| 5,176,710 A | 1/1993 | Hahn |
| 5,178,626 A | 1/1993 | Pappas |
| 5,190,547 A | 3/1993 | Barber, Jr. |
| 5,197,944 A | 3/1993 | Steele |
| 5,201,881 A | 4/1993 | Evans |
| 5,203,807 A | 4/1993 | Evans |
| 5,206,023 A | 4/1993 | Hunziker |
| 5,219,362 A | 6/1993 | Tuke |
| 5,226,916 A | 7/1993 | Goodfellow |
| 5,228,459 A | 7/1993 | Caspari |
| 5,234,432 A | 8/1993 | Brown |
| 5,234,433 A | 8/1993 | Bert |
| 5,236,432 A | 8/1993 | Matsen |
| 5,236,461 A | 8/1993 | Forte |
| 5,236,875 A | 8/1993 | Trigg |
| 5,250,050 A | 10/1993 | Poggie |
| 5,263,498 A | 11/1993 | Caspari |
| 5,269,786 A | 12/1993 | Morgan |
| 5,275,603 A | 1/1994 | Ferrante |
| 5,282,803 A | 2/1994 | Lackey |
| 5,282,867 A | 2/1994 | Mikhail |
| 5,284,482 A | 2/1994 | Mikhail |
| 5,304,181 A | 4/1994 | Caspari |
| 5,306,276 A | 4/1994 | Johnson |
| 5,314,482 A | 5/1994 | Goodfellow |
| 5,326,358 A | 7/1994 | Aubriot |
| 5,330,533 A | 7/1994 | Walker |
| 5,330,534 A | 7/1994 | Herrington |
| 5,342,368 A | 8/1994 | Peterson |
| 5,358,527 A | 10/1994 | Forte |
| 5,358,529 A | 10/1994 | Davidson |
| 5,358,531 A | 10/1994 | Goodfellow |
| 5,364,401 A | 11/1994 | Ferreante |
| 5,364,402 A | 11/1994 | Mumme |
| 5,370,699 A | 12/1994 | Hood |
| 5,370,701 A | 12/1994 | Fin |
| 5,397,330 A * | 3/1995 | Mikhail ......................... 606/88 |
| 5,405,349 A | 4/1995 | Burkinshaw |
| 5,413,604 A | 5/1995 | Hodge |
| 5,415,663 A | 5/1995 | Luckman |
| 5,417,694 A | 5/1995 | Marik |
| 5,417,695 A | 5/1995 | Axelson, Jr. |
| 5,454,816 A | 10/1995 | Ashby |
| 5,462,551 A | 10/1995 | Bailey |
| 5,470,335 A | 11/1995 | Du Toit |
| 5,474,559 A | 12/1995 | Bertin |
| 5,480,446 A | 1/1996 | Goodfellow |
| 5,514,136 A | 5/1996 | Richelsoph |
| 5,514,139 A | 5/1996 | Goldstein |
| 5,514,143 A | 5/1996 | Bonutti |
| 5,520,695 A | 5/1996 | Luckman |
| 5,540,695 A | 7/1996 | Levy |
| 5,542,947 A | 8/1996 | Treacy |
| 5,549,683 A | 8/1996 | Bonutti |
| 5,549,684 A | 8/1996 | Amino |
| 5,549,688 A | 8/1996 | Ries |
| 5,571,100 A | 11/1996 | Goble |

| | | | | | | |
|---|---|---|---|---|---|---|
| 5,578,039 | A | 11/1996 | Vendrely | 6,406,497 B2 | 6/2002 | Takei |
| 5,593,411 | A | 1/1997 | Stalcup | 6,413,279 B1 | 7/2002 | Metzger |
| 5,597,379 | A | 1/1997 | Haines | 6,430,434 B1 | 8/2002 | Mittelstadt |
| 5,601,563 | A | 2/1997 | Burke | 6,436,145 B1 | 8/2002 | Miller |
| 5,609,645 | A | 3/1997 | Vinciguerra | 6,443,991 B1 | 9/2002 | Running |
| 5,611,802 | A | 3/1997 | Samuelson | 6,458,128 B1 | 10/2002 | Schulze |
| 5,613,969 | A | 3/1997 | Jenkins, Jr. | 6,470,207 B1 | 10/2002 | Simon |
| 5,628,749 | A | 5/1997 | Vendrely | 6,475,241 B2 | 11/2002 | Pappas |
| 5,639,279 | A | 6/1997 | Burkinshaw | 6,477,400 B1 | 11/2002 | Barrick |
| 5,643,272 | A | 7/1997 | Haines | 6,482,409 B1 | 11/2002 | Lobb |
| 5,643,402 | A | 7/1997 | Schmid | 6,485,519 B2 | 11/2002 | Meyers |
| 5,649,928 | A | 7/1997 | Grundei | 6,491,699 B1 | 12/2002 | Henderson |
| 5,653,714 | A | 8/1997 | Dietz | 6,491,726 B2 | 12/2002 | Pappas |
| 5,658,293 | A | 8/1997 | Vanlaningham | 6,500,208 B1 | 12/2002 | Metzger |
| 5,667,511 | A | 9/1997 | Vendrely | 6,506,215 B1 | 1/2003 | Letot |
| 5,681,354 | A | 10/1997 | Eckhoff | 6,520,964 B2 | 2/2003 | Tallarida |
| 5,682,886 | A | 11/1997 | Delp | 6,554,838 B2 | 4/2003 | McGovern |
| 5,690,635 | A | 11/1997 | Matsen, III | 6,575,980 B1 | 6/2003 | Robie |
| 5,690,637 | A | 11/1997 | Wen | 6,579,290 B1 | 6/2003 | Hardcastle |
| 5,697,935 | A | 12/1997 | Moran | 6,595,997 B2 | 7/2003 | Axelson |
| 5,702,458 | A | 12/1997 | Burstein | 6,620,198 B2 | 9/2003 | Burstein |
| 5,723,016 | A | 3/1998 | Minns | 6,623,526 B1 | 9/2003 | Lloyd |
| 5,725,530 | A | 3/1998 | Popken | 6,645,251 B2 | 11/2003 | Salehi |
| 5,728,162 | A | 3/1998 | Eckhoff | 6,679,917 B2 | 1/2004 | Ek |
| 5,755,801 | A | 5/1998 | Walker | 6,685,711 B2 | 2/2004 | Axelson |
| 5,755,803 | A | 5/1998 | Haines | 6,694,168 B2 | 2/2004 | Traxel |
| 5,755,804 | A | 5/1998 | Schmotzer | 6,694,768 B2 | 2/2004 | Lu |
| 5,766,257 | A | 6/1998 | Goodman | 6,695,848 B2 | 2/2004 | Haines |
| 5,769,855 | A | 6/1998 | Bertin | 6,697,664 B2 | 2/2004 | Kienzle |
| 5,769,899 | A | 6/1998 | Schwartz | 6,697,768 B2 | 2/2004 | Jones et al. |
| 5,776,200 | A | 7/1998 | Johnson | 6,701,174 B1 | 3/2004 | Krause |
| 5,782,921 | A | 7/1998 | Colleran | 6,702,821 B2 | 3/2004 | Bonutti |
| 5,782,925 | A | 7/1998 | Collaz | 6,711,432 B1 | 3/2004 | Krause |
| 5,799,055 | A | 8/1998 | Peshkin | 6,725,080 B2 | 4/2004 | Melkent |
| 5,800,552 | A | 9/1998 | Forte | 6,755,563 B2 | 6/2004 | Wahlig |
| 5,810,827 | A | 9/1998 | Haines | 6,755,835 B2 | 6/2004 | Schultheiss |
| 5,824,100 | A | 10/1998 | Kester | 6,755,864 B1 | 6/2004 | Brack |
| 5,824,102 | A | 10/1998 | Buscayret | 6,672,224 B2 | 7/2004 | Tallarida |
| 5,824,105 | A | 10/1998 | Ries | 6,764,516 B2 | 7/2004 | Pappas |
| 5,871,545 | A | 2/1999 | Goodfellow | 6,770,097 B2 | 8/2004 | Leclercq |
| 5,871,546 | A | 2/1999 | Colleran | 6,773,461 B2 | 8/2004 | Meyers |
| 5,879,354 | A | 3/1999 | Haines | 6,783,550 B2 | 8/2004 | MacArthur |
| 5,879,392 | A | 3/1999 | McMinn | 6,796,988 B2 | 9/2004 | Melkent |
| 5,906,643 | A | 5/1999 | Walker | 6,827,723 B2 | 12/2004 | Carson |
| 5,908,424 | A | 6/1999 | Bertin | 6,858,032 B2 | 2/2005 | Chow |
| 5,935,173 | A | 8/1999 | Roger | 6,875,222 B2 | 4/2005 | Long |
| 5,954,770 | A | 9/1999 | Schmotzer | 6,886,684 B2 | 5/2005 | Hacikyan |
| 5,980,526 | A | 11/1999 | Johnson | 6,898,858 B2 | 5/2005 | Spell |
| 5,986,169 | A | 11/1999 | Gjunter | 6,911,044 B2 | 6/2005 | Fell |
| 5,997,577 | A | 12/1999 | Herrington | 6,916,324 B2 | 7/2005 | Sanford |
| 6,039,764 | A | 3/2000 | Pottenger et al. | 6,916,340 B2 | 7/2005 | Metzger |
| 6,056,754 | A | 5/2000 | Haines | 6,942,627 B2 | 9/2005 | Huitema |
| 6,059,788 | A | 5/2000 | Katz | 6,942,694 B2 | 9/2005 | Liddicoat |
| 6,068,658 | A | 5/2000 | Insall | 7,018,418 B2 | 3/2006 | Amrich |
| 6,080,195 | A | 6/2000 | Colleran | 7,029,477 B2 | 4/2006 | Grimm |
| 6,099,570 | A | 8/2000 | Livet | 7,048,741 B2 | 5/2006 | Swanson |
| 6,120,543 | A | 9/2000 | Meesenburg | 7,077,867 B2 | 7/2006 | Pope |
| 6,132,468 | A | 10/2000 | Mansmann | 7,104,966 B2 | 9/2006 | Shilber |
| 6,139,581 | A | 10/2000 | Engh | 7,104,996 B2 | 9/2006 | Bonutti |
| 6,165,223 | A | 12/2000 | Metzger | 7,141,053 B2 | 11/2006 | Rosa |
| 6,171,340 | B1 | 1/2001 | McDowell | 7,172,596 B2 | 2/2007 | Coon |
| 6,197,064 | B1 | 3/2001 | Haines | 7,175,630 B2 | 2/2007 | Farling |
| 6,203,576 | B1 | 3/2001 | Afriat | 7,241,298 B2 | 7/2007 | Nemec |
| 6,206,926 | B1 | 3/2001 | Pappas | 7,247,157 B2 | 7/2007 | Prager |
| 6,210,443 | B1 | 4/2001 | Marceaux | 7,326,252 B2 | 2/2008 | Otto |
| 6,235,060 | B1 | 5/2001 | Meesenburg | 7,344,541 B2 | 3/2008 | Haines |
| 6,236,875 | B1 | 5/2001 | Becholz | 7,371,240 B2 | 5/2008 | Pinczewski |
| 6,264,697 | B1 | 7/2001 | Walker | 7,422,605 B2 | 9/2008 | Burstein |
| 6,285,902 | B1 | 9/2001 | Kienzle | 7,491,235 B2 | 2/2009 | Fell |
| 6,306,172 | B1 | 10/2001 | O'Neil | 7,922,771 B2 | 4/2011 | Otto |
| 6,325,828 | B1 | 12/2001 | Dennis | 2001/0018615 A1 | 8/2001 | Biegun |
| 6,340,363 | B1 | 1/2002 | Bolger | 2001/0044627 A1 | 11/2001 | Justin |
| 6,342,075 | B1 | 1/2002 | MacArthur | 2001/0049558 A1 | 12/2001 | Liddicoat |
| 6,348,058 | B1 | 2/2002 | Melkent | 2002/0055784 A1 | 5/2002 | Burstein |
| 6,361,564 | B1 | 3/2002 | Marceaux | 2002/0103541 A1 | 8/2002 | Meyers |
| 6,368,353 | B1 | 4/2002 | Arcand | 2002/0107576 A1 | 8/2002 | Meyers |
| 6,375,658 | B1 | 4/2002 | Hangody | 2002/0120340 A1 | 8/2002 | Metzger |
| 6,379,388 | B1 | 4/2002 | Ensign | 2002/0161447 A1 | 10/2002 | Salehi |
| 6,401,346 | B1 | 6/2002 | Roberts | 2002/0198531 A1* | 12/2002 | Millard et al. .......... 606/87 |

| | | | |
|---|---|---|---|
| 2003/0028196 A1 | 2/2003 | Bonutti | |
| 2003/0055501 A1 | 3/2003 | Fell | |
| 2003/0055509 A1 | 3/2003 | McCue | |
| 2003/0060882 A1 | 3/2003 | Fell | |
| 2003/0060883 A1 | 3/2003 | Fell | |
| 2003/0060884 A1 | 3/2003 | Fell | |
| 2003/0060885 A1 | 3/2003 | Fell | |
| 2003/0069585 A1 | 4/2003 | Axelson | |
| 2003/0069591 A1 | 4/2003 | Carson | |
| 2003/0093156 A1 | 5/2003 | Metzger | |
| 2003/0130665 A1 | 7/2003 | Pinczewski | |
| 2003/0181986 A1 | 9/2003 | Buchholz | |
| 2003/0208122 A1 | 11/2003 | Melkent | |
| 2003/0212413 A1 | 11/2003 | Wilk | |
| 2004/0039396 A1 | 2/2004 | Couture | |
| 2004/0044414 A1 | 3/2004 | Nowakowski | |
| 2004/0122305 A1 | 6/2004 | Grimm | |
| 2004/0152970 A1 | 8/2004 | Hunter | |
| 2004/0153066 A1 | 8/2004 | Coon | |
| 2004/0199249 A1 | 10/2004 | Fell | |
| 2004/0199250 A1 | 10/2004 | Fell | |
| 2004/0249467 A1 | 12/2004 | Meyers | |
| 2004/0249471 A1 | 12/2004 | Bindseil | |
| 2004/0267363 A1 | 12/2004 | Fell | |
| 2005/0033424 A1 | 2/2005 | Fell | |
| 2005/0149038 A1 | 7/2005 | Haines | |
| 2005/0149039 A1 | 7/2005 | Haines | |
| 2005/0149040 A1 | 7/2005 | Haines | |
| 2005/0171604 A1 | 8/2005 | Michalow | |
| 2006/0015109 A1 | 1/2006 | Haines | |
| 2006/0015115 A1 | 1/2006 | Haines | |
| 2006/0015116 A1 | 1/2006 | Haines | |
| 2006/0015117 A1 | 1/2006 | Haines | |
| 2006/0030853 A1 | 2/2006 | Haines | |
| 2006/0030854 A1 | 2/2006 | Haines | |
| 2006/0030855 A1 | 2/2006 | Haines | |
| 2006/0030944 A1 | 2/2006 | Haines | |
| 2006/0052875 A1 | 3/2006 | Bernero | |
| 2006/0058882 A1 | 3/2006 | Haines | |
| 2007/0078517 A1 | 4/2007 | Engh | |
| 2007/0179607 A1 | 8/2007 | Hodorek | |
| 2008/0154270 A1* | 6/2008 | Haines et al. ............... | 606/88 |
| 2009/0076514 A1 | 3/2009 | Haines | |
| 2009/0082773 A1 | 3/2009 | Haines | |
| 2010/0100192 A1 | 4/2010 | Haines | |
| 2010/0191244 A1* | 7/2010 | White et al. ............... | 606/88 |

FOREIGN PATENT DOCUMENTS

| | | |
|---|---|---|
| EP | 0121142 | 10/1984 |
| EP | 0189253 | 7/1986 |
| EP | 0243109 | 10/1987 |
| EP | 0327249 | 8/1989 |
| EP | 0337901 | 10/1989 |
| EP | 0380451 | 1/1990 |
| EP | 0941719 | 9/1990 |
| EP | 0415837 | 3/1991 |
| EP | 0466659 A2 | 1/1992 |
| EP | 0538153 A1 | 4/1993 |
| EP | 0555003 | 8/1993 |
| EP | 556998 | 8/1993 |
| EP | 0682916 A2 | 11/1995 |
| EP | 0761242 | 3/1997 |
| EP | 0916321 | 5/1999 |
| EP | 0923916 | 6/1999 |
| EP | 0970667 | 1/2000 |
| EP | 0988840 | 3/2000 |
| FR | 2635675 | 3/1990 |
| FR | 2664157 A1 | 1/1992 |
| FR | 2701387 | 8/1994 |
| FR | 2710258 | 3/1995 |
| FR | 2760352 | 9/1998 |
| GB | 1409150 | 10/1975 |
| GB | 2007980 | 7/1982 |
| GB | 2296443 | 7/1996 |
| GB | 2324249 | 10/1998 |
| GB | 2335145 | 9/1999 |
| JP | 02-501806 | 1/1983 |
| JP | 58-209343 | 12/1983 |
| JP | 61-170453 | 8/1986 |
| JP | 62-133948 | 6/1987 |
| JP | 62-254750 | 6/1987 |
| JP | 01-119244 | 5/1989 |
| JP | 01-126957 | 5/1989 |
| JP | 01-209055 | 8/1989 |
| JP | 02-057247 | 2/1990 |
| JP | 02-234756 | 9/1990 |
| JP | 02-234757 | 9/1990 |
| JP | 02-243143 | 9/1990 |
| JP | 239861 | 9/1990 |
| JP | 02-246971 | 10/1990 |
| JP | 2002/274214 | 11/1990 |
| JP | 03-032663 | 2/1991 |
| JP | 04-297254 | 10/1992 |
| JP | 04-361746 | 12/1992 |
| JP | 05-003880 | 1/1993 |
| JP | 05-502814 | 5/1993 |
| JP | 5-41510 | 6/1993 |
| JP | 05-269140 | 10/1993 |
| JP | 05-277130 | 10/1993 |
| JP | 06-08033 | 1/1994 |
| JP | 06-38971 | 2/1994 |
| JP | 6-217984 | 8/1994 |
| JP | 06-233775 | 8/1994 |
| JP | 06-233941 | 8/1994 |
| JP | 7-501966 | 3/1995 |
| JP | 7-116185 | 5/1995 |
| JP | 7-136200 | 5/1995 |
| RU | 2121319 | 11/1998 |
| SE | 382155 | 1/1976 |
| SU | 577020 T | 10/1977 |
| WO | WO 81/03122 | 11/1981 |
| WO | WO 91/00061 | 1/1991 |
| WO | WO 91/10408 | 7/1991 |
| WO | WO 93/22990 | 11/1993 |
| WO | WO 93/25157 | 12/1993 |
| WO | WO 94/05212 | 3/1994 |
| WO | WO 94/08528 | 4/1994 |
| WO | WO 94/09730 | 5/1994 |
| WO | WO 94/14366 | 7/1994 |
| WO | WO 94/22397 | 10/1994 |
| WO | WO96/01588 | 1/1996 |
| WO | WO96/07361 A1 | 3/1996 |
| WO | WO 96/24295 | 8/1996 |
| WO | WO 97/05827 | 2/1997 |
| WO | WO97/29703 A1 | 8/1997 |
| WO | WO97/29704 A1 | 8/1997 |
| WO | WO 9820817 | 5/1998 |
| WO | WO 99/27872 | 6/1999 |
| WO | WO 99/30649 | 6/1999 |
| WO | WO 01/13825 | 3/2001 |
| WO | WO02/34310 | 5/2002 |
| WO | WO2004/069036 | 8/2004 |
| WO | WO2004/070580 | 8/2004 |
| WO | WO2004/100758 | 11/2004 |
| WO | WO2004/100839 | 11/2004 |

OTHER PUBLICATIONS

E. Marlowe Goble and Daniel F. Justin, *Minimally invasive total knee replacement: principles and technique*, Orthop. Clin. N. Am. 35 (2004) 235-245.

Whiteside Ortholoc Total Knee System: Surgical Procedure, Dow Corning Wright, pp. WMT000001-WMT000040, Jun. 1985.

Zimmer, Insall/Burstein II, *Constrained Condylar: Modular Knee System*, Surgical Technique, 35 pages, copyright 1989.

File History for U.S. Appl. No. 11/075,842, filed Mar. 8, 2005.
File History for U.S. Appl. No. 11/075,828, filed Mar. 8, 2005.
File History for U.S. Appl. No. 11/075,836, filed Mar. 8, 2005.
U.S. Appl. No. 12/171,843, Inventor: Haines, filed Jul. 11, 2008.
U.S. Appl. No. 11/036,584, Inventor: Haines, filed Jan. 14, 2005.
File History for U.S. Appl. No. 11/075,840, filed Mar. 8, 2005.
U.S. Appl. No. 11/075,552, Inventor: Haines, filed Mar. 8, 2005.
File History for U.S. Appl. No. 11/049,634, filed Feb. 5, 2005.
File History for U.S. Appl. No. 11/074,599, filed Mar. 8, 2005.
File History for U.S. Appl. No. 11/075,553, filed Mar. 8, 2005.
U.S. Appl. No. 11/825,857, Inventor: Haines, filed Jul. 9, 2007.

Zimmer, Insall/Burnstein II, *Modular Knee System*, Surgical Technique, pp. ZH000109691-ZH000109710.

Zimmer, The Miller/Galante Advantage: Total Knee System, pp. ZH000156953-ZH000156968.

Whiteside Ortholoc Total Knee System, Dow Corning Wright, pp. ZH000109679-ZH000109690.

Freeman Samuelson, *Total Knee System*, published by Biomet, Inc., 1994 ("Biomet Brochure") (Attached as Exhibit F).

Freeman, Mark II *Total Knee Replacement System*, published 1985 (Attached as Exhibit G).

Protek F/S Modular Total Knee Replacement System, pp. 1-57, published by Protek in Jan. 1991 (Attached as Exhibit H).

*Low Contact Stress Meniscal Bearing Unicompartmental Knee Replacement: Long-Term Evaluation of Cemented and Cementless Results*, Journal of Orthopaedic Rheumatology (presented at the 57th Annual American Academy of Orthpaedic Surgeons Meetings, New Orleans, LA, Feb. 11, 1990), Bates No. DEP00004096-DEP00004107.

N.J. Unicompartmental Knee, Dated Sep. 15, 1989, Bates No. DEP00004108-DEP00004116.

Buechel, Frederick F., *NJ LCS Unicompartmental Knee System with Porocoat*, dated Oct. 24, 1994, Bates No. DEP000004117-DEP00004130.

Buechel, Frederick F. *NJ LCS Unicompartmental Knee System with Porocoat*, 1994, Bates No. DEP00004131-DEP00004141.

Buechel, Frederick F. *NJ LCS Unicompartmental Knee System with Porocoat*, 1994, Bates No. DEP00004142-DEP00004152.

Engh, et al., *The AMK Total Knee System, Design Rationale and Surgical Procedure*, dated 1989, Bates No. DEP00004153-DEP00004201.

*Advertising Proteck Mark II PCR Total Knee Replacement System*, Journal of Bone and Joint Surgery, 1987, Bates No. DEP00004202-DEP00004230.

Protek, *Parts Brochure for Mark II Protek*, 1987, Bates No. DEP00004231-DEP00004235.

Chapman, Michael W., *Operative Orthopaedics*, vol. 1, Published by J.B. Lipponcott Co., Philadelphia, dated 1988, Bates No. DEP00004236-DEP00004247.

American Academy of Orthopaedic Surgeons, *Flyer from 57th Annual American Academy of Orthopaedic Surgeons Meeting*, Feb. 13, 1990, Bates No. DEP00004248-DEP00004251.

Crossett et al., *AMK Congruency Instrument System, Surgical Technique*, dated 1997, Bates No. DEP00004252-DEP00004267.

Engh et al., *AMK Surgical Technique*, Bates No. DEP00004268-DEP00004298, dated 1989.

Engh et al., *AMK Surgical Technique*, Bates No. DEP00004299-DEP0004329, dated 1989.

Crenshaw, A.H., *Campbell's Operative Orthopaedics*, 4th Edition, vol. 1, Bates No. DEP00004330-DEP00004333, dated 1963.

Howmedica, *Duraconcept, Design Concepts of the Duracon Total Knee System*, Bates No. DEP00004337-DEP00004337, dated 1993.

Freeman et al., *Total Knee System*, Bates No. DEP00004350-DEP00004361, Published prior to Jun. 7, 1994.

Freeman et al., *F/S Modular Total Knee Replacement System—SICOT*, 90 Edition, Bates No. DEP00004362-DEP00004373, dated 1990.

Buechel, Frederick F., *Howmedica Product Catalog*, Bates No. DEP00004374-DEP00004375, dated 1994.

Massarella, Antony, *Interax Bulletin, No. 6, Tibial Intramedullary Alignment Surgical Technique*, Bates No. DEP00004387-DEP0000-4390, dated Feb. 23, 1994.

Desjardins et al., *Interax Operative Technique*, Bates No. DEP00004391-DEP00004411, dated 1994.

Desjardins et al., *Interax Total Knee Operative Technique: Monogram Total Knee Instruments*, Bates No. DEP00004412-DEP00004432, dated 1993.

Howmedica, *Interax Tibial IM*, Bates No. DEP00004433-DEP00004433, dated 1994.

Depuy, *LCS Uni PMA Data from FDA Website*, Bates No. DEP00004434-DEP00004434, dated 1991.

Briard et al., *LCS Uni Unicompartmental Knee System with Porocoat*, Bates No. DEP00004452-DEP00004462, dated 1991.

Freeman et al., *Mark II Total Knee Replacement System*, Bates No. DEP00004463-DEP00004492, dated 1985.

Buechel, Frederick F., *NJ LCS Unicompartmental Knee System with Porocoat*, Bates No. DEP00004493-DEP00004503, dated 1994.

Chapman, Michael W. *Operative Orthopaedics*, vol. 3, 2nd Edition, Published by J.B. Lipponcott Co., Bates No. DEP00004504-DEP00004508, dated 1993.

Biomet, *Oxford Meniscal Knee Phase II Unicompartmental Replacement*, Bates No. DEP00004509-DEP00004515, Published prior to Jun. 7, 1994.

Scott et al., *P.F.C. Sigma Unicompartmental Knee System*, Bates No. DEP00004531-DEP00004539, dated 1998.

Freeman et al., *F/S Modular Total Knee Replacement System*, Bates No. DEP00004540-DEP00004596, dated 1990.

Broughton et al., *Unicompartmental Replacement and High Tibial Osteotomy for Osteoarthritis of the Knee*, Journal of Bone and Joint Surgery, vol. 68-B, No. 3, May 1, 1986, pp. 447-452, Bates No. DEP00004752-DEP00004763.

Scott et al., *Unicompartmental and High Tibial Osteotomy for Osteoarthritis of the Knee*, Journal of Bone and Joint Surgery, vol. 63-A, No. 4, Apr. 1, 1981, Bates No. DEP00004764-DEP00004775.

Thornhill, Thomas S., *Unicompartmental Knee Arthroplasty Clinical Orthopaedics and Related Research*, No. 205, Apr. 1, 1986, pp. 121-131, Bates No. DEP00004776-DEP00004791.

Forst et al., *A Special jg for Tibial Resection for the Implantation of GSB-Knee-Prostheses in Problematic cases*, pp. 162-166, dated Jun. 1, 1984, Bates No. DEP00004838-DEP00004842.

Ingillis et al., *Revision Total Knee Replacement Techniques in Orthopedics*, dated Apr. 1, 1990, Bates No. DEP00005583-DEP00005592.

Uvehammer et al., "In Vivo Kinematics of Total Knee Arthroplasty: Concave Versus Posterior-Stabilised Tibial Joint Surface", vol. 82-B, No. 4, May 2000, pp. 499-505.

\* cited by examiner

Fig. 3A FEMUR

Fig. 3B TIBIA

PATELLA

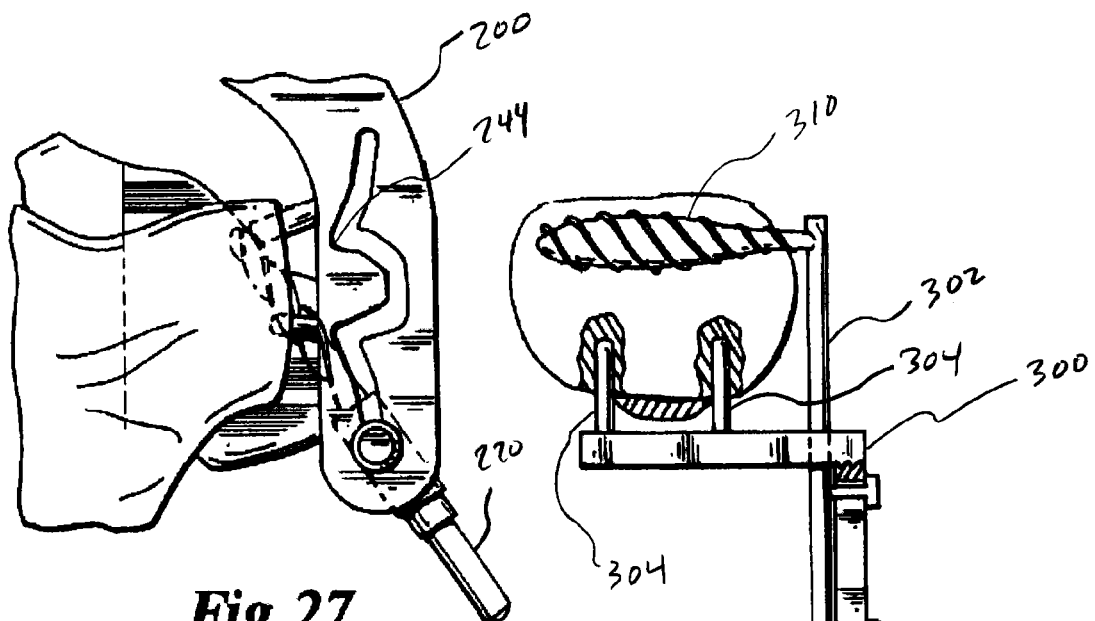
*Fig.27*
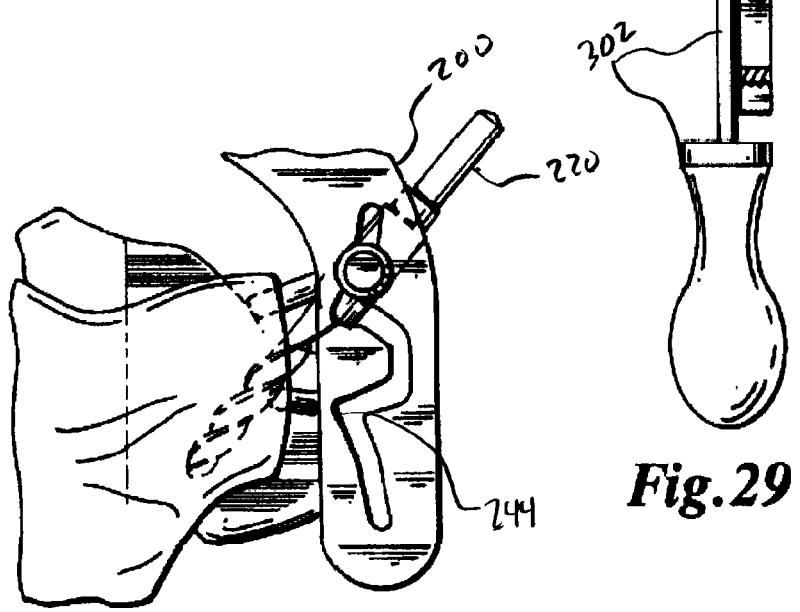
*Fig.28*
*Fig.29*

METHODS AND APPARATUS FOR PIVOTABLE GUIDE SURFACES FOR ARTHROPLASTY

CLAIM TO PRIORITY

The present invention claims priority to U.S. Provisional Application No. 60/551,080, filed Mar. 8, 2004, entitled, "METHODS AND APPARATUS FOR PIVOTABLE GUIDE SURFACES FOR ARTHROPLASTY," and U.S. Provisional Application No. 60/551,078, filed Mar. 8, 2004, entitled, "METHODS AND APPARATUS FOR MINIMALLY INVASIVE RESECTION," and U.S. Provisional Application No. 60/551,096, filed Mar. 8, 2004, entitled, "METHODS AND APPARATUS FOR ENHANCED RETENTION OF PROSTHETIC IMPLANTS," and U.S. Provisional Application No. 60/551,631, filed Mar. 8, 2004, entitled, "METHODS AND APPARATUS FOR CONFORMABLE PROSTHETIC IMPLANTS," and U.S. Provisional Application No. 60/551,307, filed Mar. 8, 2004, entitled, "METHODS AND APPARATUS FOR IMPROVED CUTTING TOOLS FOR RESECTION," and U.S. Provisional Application No. 60/551,262, filed Mar. 8, 2004, entitled, "METHODS AND APPARATUS FOR IMPROVED DRILLING AND MILLING TOOLS FOR RESECTION," and U.S. Provisional Application No. 60/551,160, filed Mar. 8, 2004, entitled, "METHODS AND APPARATUS FOR IMPROVED PROFILE BASED RESECTION," and U.S. patent application Ser. No. 11/036,584, filed Jan. 14, 2005, entitled, "METHODS AND APPARATUS FOR PINPLASTY BONE RESECTION," which claims priority to U.S. Provisional Application No. 60/536,320, filed Jan. 14, 2004, and U.S. patent application Ser. No. 11/049,634, filed Feb. 3, 2005, entitled, "METHODS AND APPARATUS FOR WIREPLASTY BONE RESECTION," which claims priority to U.S. Provisional Application No. 60/540,992, filed Feb. 2, 2004, entitled, "METHODS AND APPARATUS FOR WIREPLASTY BONE RESECTION," the entire disclosures of which are hereby fully incorporated by reference.

BACKGROUND OF THE INVENTION

1. Field of the Invention

This invention generally relates to methods and apparatus for bone resection to allow for the interconnection or attachment of various prosthetic devices with respect to the patient. More particularly, the present invention relates to the use of pivotable guide surfaces for arthroplasty and bone resection techniques.

2. Background Art

Different methods and apparatus have been developed in the past to enable a surgeon to remove bony material to create specifically shaped surfaces in or on a bone for various reasons including to allow for attachment of various devices or objects to the bone. Keeping in mind that the ultimate goal of any surgical procedure is to restore the body to normal function, it is critical that the quality and orientation of the cut, as well as the quality of fixation, and the location and orientation of objects or devices attached to the bone, is sufficient to ensure proper healing of the body, as well as appropriate mechanical function of the musculoskeletal structure.

In total knee replacements, for example, a series of planar and/or curvilinear surfaces, or "resections," are created to allow for the attachment of prosthetic or other devices to the femur, tibia and/or patella. In the case of the femur, it is common to use the central axis of the femur, the posterior and distal femoral condyles, and/or the anterior distal femoral cortex as guides to determine the location and orientation of distal femoral resections. The location and orientation of these resections are critical in that they dictate the final location and orientation of the distal femoral implant. It is commonly thought that the location and orientation of the distal femoral implant are critical factors in the success or failure of the artificial knee joint. Additionally, with t any surgical procedure, time is critical, and methods and apparatus that can save operating room time, are valuable. Past efforts have not been successful in consistently and/or properly locating and orienting resections in a quick and efficient manner.

Early techniques for bone resection involved the drilling of location holes into the bone to be resected and then pinning a guide plate in a fixed position to the bone using these holes as shown, for example, in U.S. Pat. No. 4,718,413. The guide plate would include guide surfaces or guide slots for a guiding a planar oscillating saw blade to aid the surgeon in resecting the bone surfaces. Some guide plates have utilized guide pin slots that cooperate with retractable guide pins on the oscillating saw to define a path for moving the saw as described, for example, in U.S. Pat. No. 5,092,869. The need to insure proper orientation of the guide mechanism relative to the long access of the femur, for example, led to the generally accepted practice of inserting a long rod into the intermedullary canal within the femur as a fixed point of reference for the guide mechanism. U.S. Pat. No. 5,047,032 describes a resection technique that uses an intermedullary rod as a fixed pivot point for a milling bit or router that resects a circular path around the intermedullary rod in order to create a single resected surface on the end of the femur. U.S. Pat. Nos. 5,228,459, 5,571,100 and 5,653,714 and U.S. Publ. Appl. 2003/0045883A1 describe various resection guide systems in which some portion of the guide mechanism can be rotated into a desired position and then locked in that position to permit the guide mechanism to be aligned by the surgeon in multiple different fixed positions. U.S. Pat. No. 5,643,272, for example, describes embodiments of a profile based resection technique that utilizes guide surfaces that permit the surgeon to plunge and sweep the cutting profile of a cutting tool in an arc within the confines of the guide surfaces.

While the cutting profile of the cutting tool is retained in a plane defined by the guide surfaces, there is no guide for how the surgeon manipulates the cutting tool in a sweeping manner to define the arc(s) within that plane.

SUMMARY OF THE INVENTION

The present invention provides for embodiments of cutting guides, cutting tools, and soft tissue management techniques that permit the use of pivoting guide surfaces to facilitate in controlling the sweep or arc of a cutting tool used in connection with resection and arthroplasty procedures. In accordance with the present invention, a guide structure is provided with one or more guide pivot aperture(s) and one or more guide pivot reference surface(s) that mate with a bushing assembly controlling a cutting tool. The bushing assembly possesses a bushing reference plane (which mates with the pivot reference surface(s) of the guide structure) and a bushing pivot pin (which mates with the guide pivot aperture(s) of the guide structure). In one embodiment, a cannulation mechanism is operably coupled to the guide structure for articulated and/or axial guidance of the cutting tool.

The present invention utilizes a number of embodiments of cutting guide technologies loosely or directly based on Profile Based Resection (PBR). Preferably, the present invention is utilized for creating planar and/or curvilinear resection surfaces on or in the proximal tibial and other bones for prosthetic implants. The overriding objects of PBR technologies are to provide for significantly improved reproducibility of implant fit and alignment in a manner largely independent of the individual surgeon's manual skills, while providing for outstanding ease of use, economic, safety, and work flow performance.

The present invention may be utilized with a number of embodiments of alignment or drill guides to precisely and accurately determine the desired cutting guide location/orientation. In one embodiment, the guide structure is secured to the bone to be resected by fixation pins, although other techniques for referencing and aligning the guide structure are also encompassed by the present invention. The overriding objects of the embodiments are to precisely and accurately dictate the aforementioned locations and orientations while optionally enabling ease of use in conjunction with manually or Computer Assisted techniques, and while preferably enabling ease of use in minimally invasive procedures where surgical exposure and trauma are minimized.

The present invention utilizes a number of embodiments of cutting tools to remove bony material to create cut surfaces for prosthetic implant attachment and fixation. The overriding objects of the embodiments are to provide the ability to perform resection in very small incisions, the creation of precise and accurate cut(s), and to provide for soft tissue protection characteristics and features preventing the tool from accidentally harming soft tissue. Specifically, many of the cutting tool embodiments disclosed are either incapable or highly resistant to damaging soft tissue, or are by means disclosed prevented from coming into contact with soft tissue in the first place.

The present invention utilizes a number of methods and apparatus embodiments of soft tissue management techniques and the devices supporting said techniques. The overriding object of these embodiments is to take advantage of the anatomy, physiology, and kinematics of the human body in facilitating clinical efficacy of orthopedic procedures.

It is an often repeated rule of thumb for orthopedic surgeons that a "Well placed, but poorly designed implant will perform well clinically, while a poorly placed, well designed implant will perform poorly clinically." The present invention provides a method and apparatus for reducing implant placement errors in order to create more reproducible, consistently excellent clinical results in a manner that decreases risk to soft tissue, incision or exposure size requirements, manual skill requirements, and/or visualization of cutting action.

It should be clear that applications of the present invention is not limited to Total Knee Arthroplasty or the other specific applications cited herein, but are rather universally applicable to any form of surgical intervention where the resection of bone is required. These possible applications include, but are not limited to Unicondylar Knee Replacement, Hip Arthroplasty, Ankle Arthroplasty, Spinal Fusion, Osteotomy Procedures (such as High Tibial Osteotomy), ACL or PCL reconstruction, and many others. In essence, any application where an expense, accuracy, precision, soft tissue protection or preservation, minimal incision size or exposure are required or desired for a bone resection and/or prosthetic implantation is a potential application for this technology. In addition, many of the embodiments shown have unique applicability to minimally invasive surgical (MIS) procedures and/or for use in conjunction with Surgical Navigation, Image Guided Surgery, or Computer Aided Surgery systems.

BRIEF DESCRIPTION OF THE DRAWINGS

Other important objects and features of the invention will be apparent from the following detailed description of the invention taken in connection with the accompanying drawings in which:

FIGS. 1, 2, and 3 are pictorial representations standard incision sizes or exposure required by the prior art, while

FIGS. 5-50 show various depictions of embodiments and methods in accordance with alternate embodiments of the present invention.

DETAILED DESCRIPTION OF THE PREFERRED EMBODIMENTS

It should be noted that, in many of the figures, the cut surface created by the cutting tool in accordance with the techniques of the present invention are shown as having already been completed for the sake of clarity. Similarly, the bones may be shown as being transparent or translucent for the sake of clarity. The guides/pins, cutting tool, bones, and other items disclosed are may be similarly represented for the sake of clarity or brevity FIGS. 1 T*hrough* 4

Figure 1:
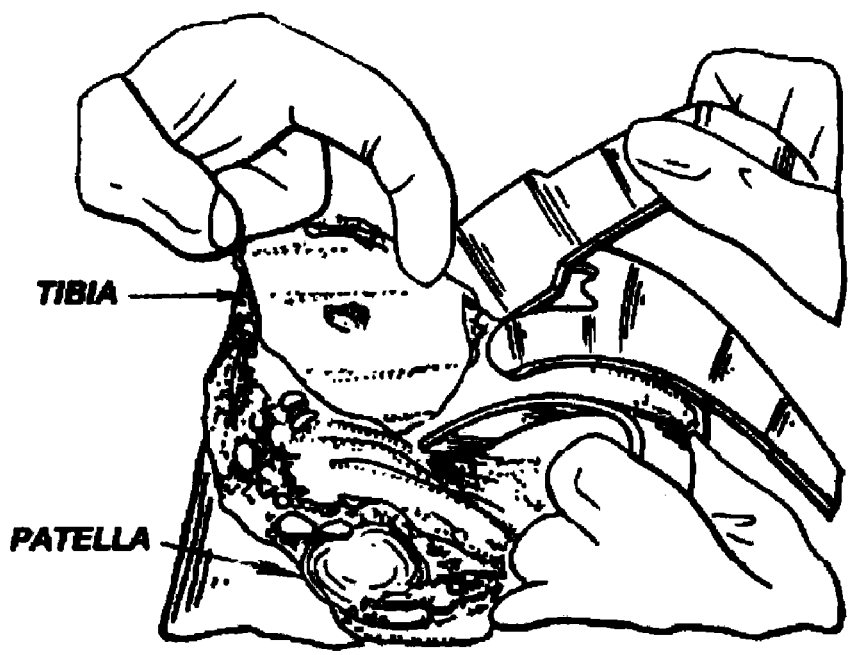
Figure 2:
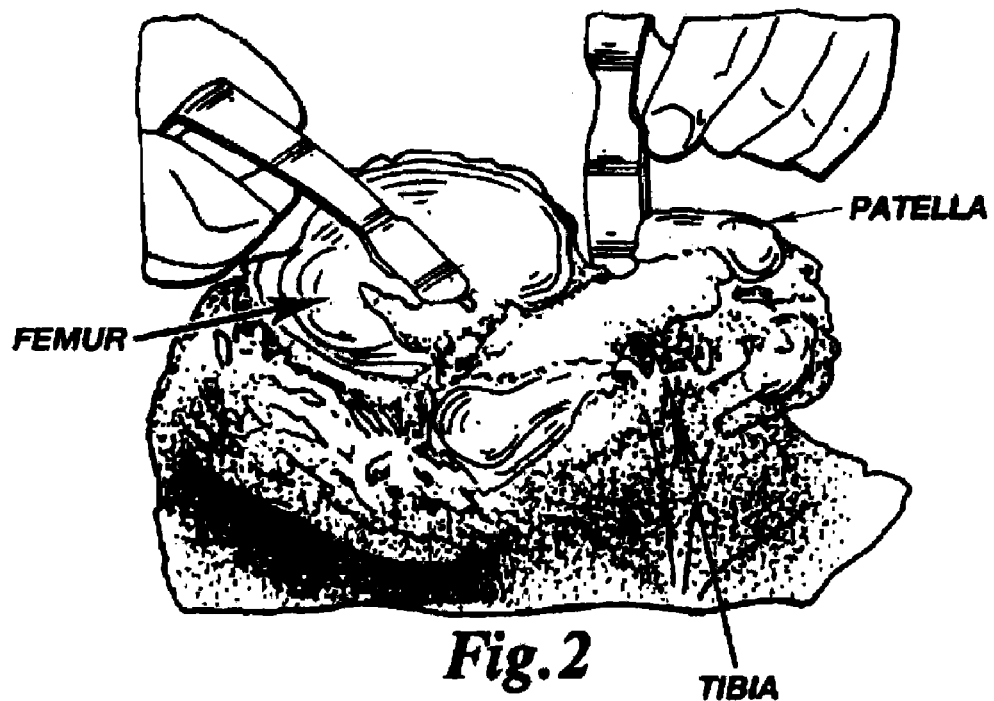
Figure 3C:
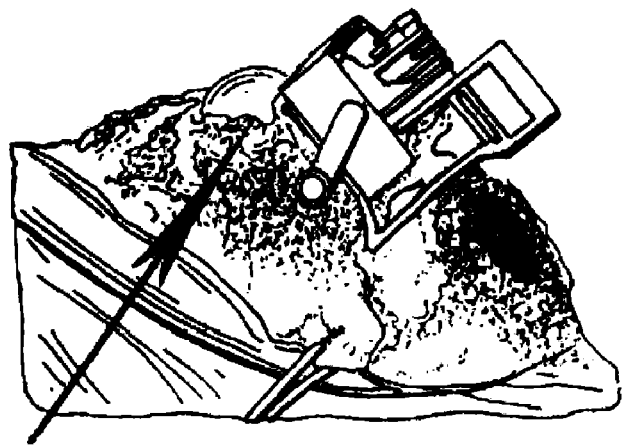
Figure 3C:
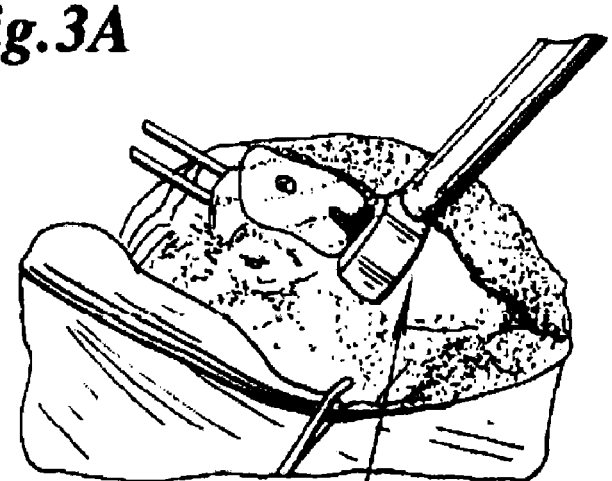
Figure 3C:
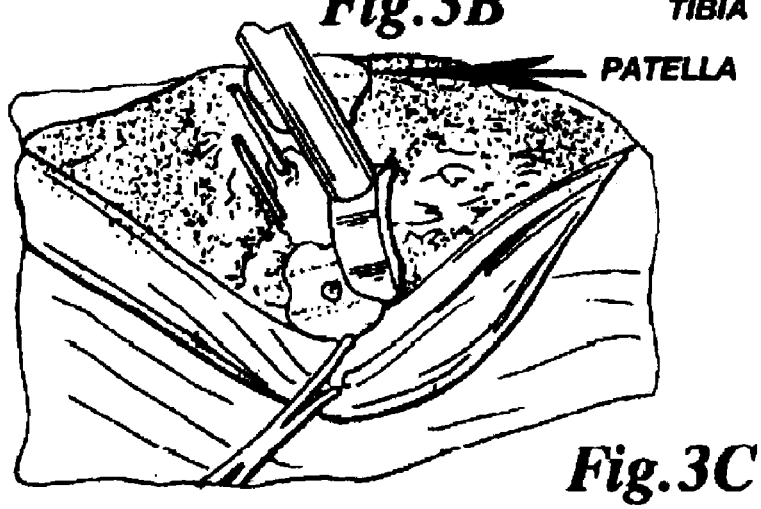
Figure 4:
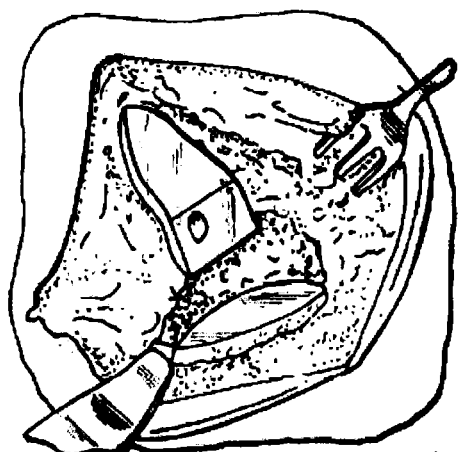
FIG. 4 is a pictorial representation or approximation of one form of surgical exposure that is desired.

FIGS. 1 and 2 show conventional surgical exposures and instrumentation being utilized. FIG. 4 shows a reduced incision currently utilized in performing the current state of the art in 'minimally invasive' Unicondylar Knee Replacement.

Figure 5:
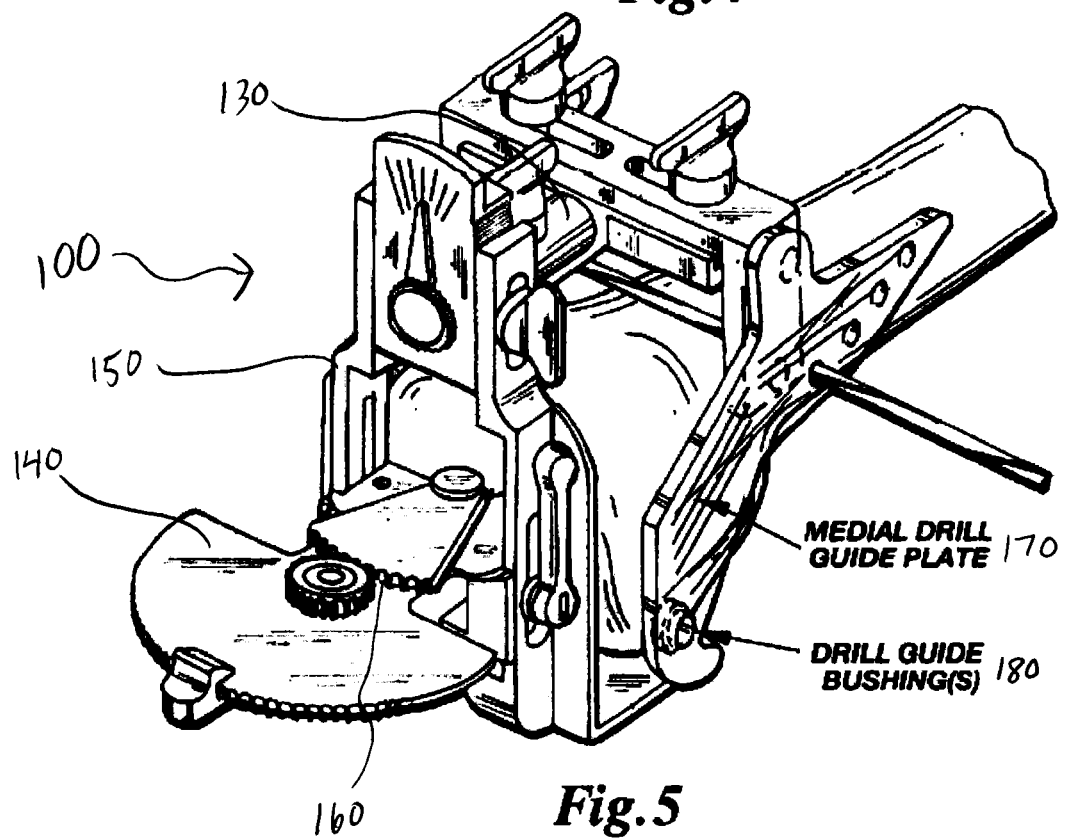

FIGS. 5 T*hrough* 11

Figure 6:
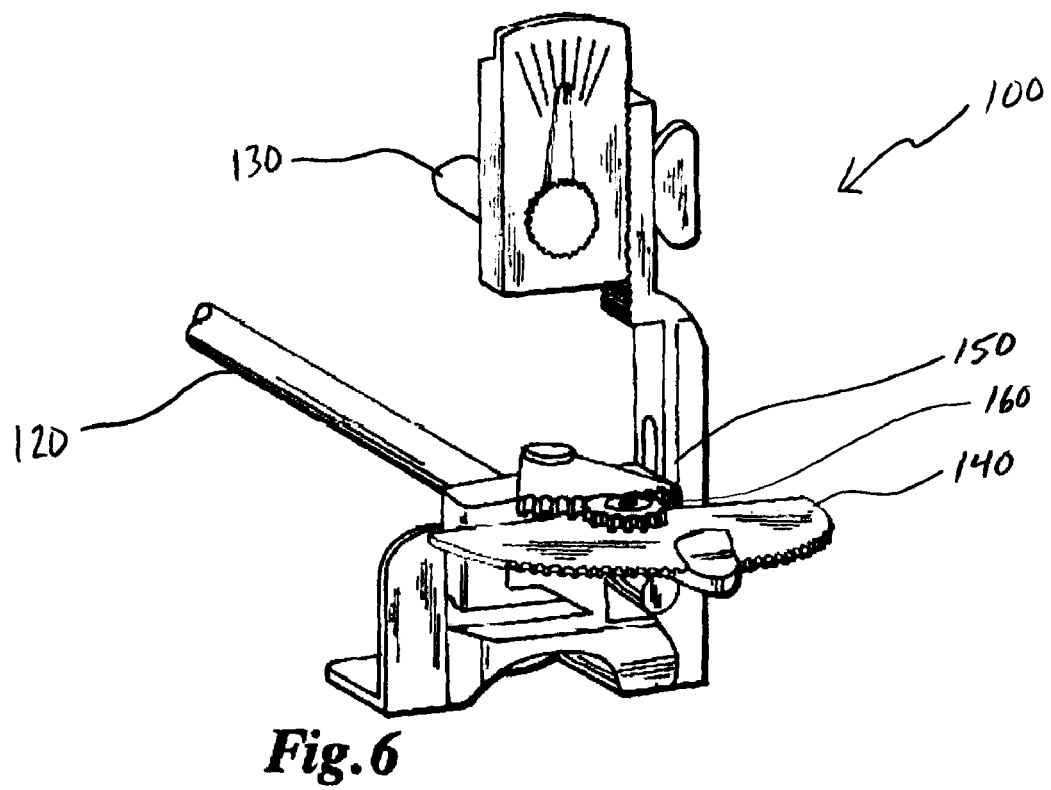
Figure 7:
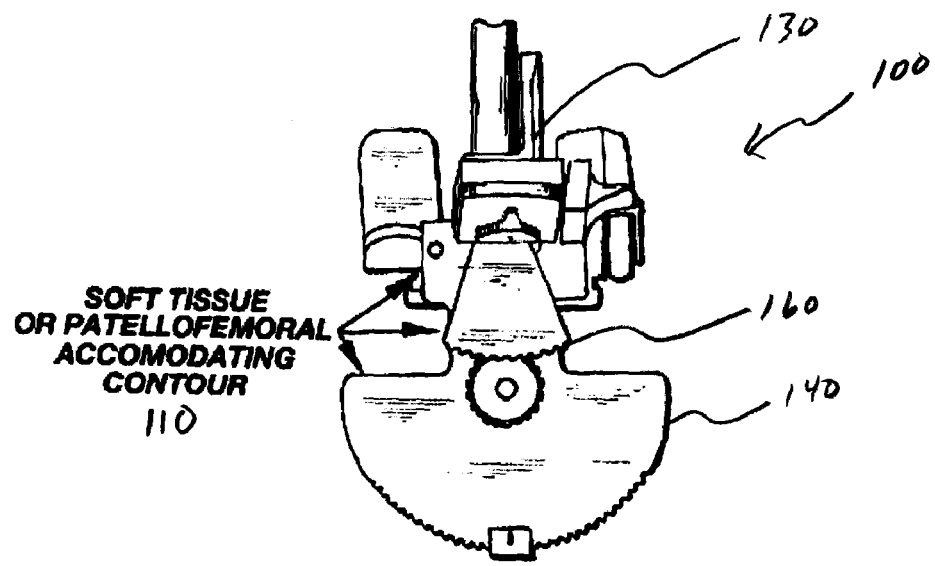

FIGS. 5 through 11 describe an alignment guide/drill guide apparatus 100 and/or drill guide/alignment guide techniques that can be used in conjunction with the present invention to align and secure the guide assembly via alignment pins, FIG. 5 shows a manually operated alignment guide 100 suitable for use with surgical exposures similar to that shown in FIG. 2 (it should be noted that surgical navigation sensors could be used to assist in determining final drill guide location and orientation). FIGS. 6 and 7 show an improvement upon the embodiment shown in FIG. 5 for enabling manual alignment guide 100 use in less invasive incisions by providing soft tissue accommodating contours or reliefs 110. In other words, for a medial parapatellar incision, the alignment guide 100 is configured to allow for appropriate contact and referencing of the distal and posterior femoral condyles, the IM canal (when not relying on an extramedullary reference or inference of the mechanical axis) or IM Rod 120, the anterior cortex or anterior runout point of a given or proposed implant size (via a stylus not shown), and the epicondylar axis via palpitation or visual reference while the patellar tendon, patella, and/or quadriceps tendon are draped over or accommodated within the lateral side (left side as shown in the figures) of the alignment guide 100 allowing insertion of the guide when the patella is neither everted not fully dislocated as in conventional techniques. It should be noted that initial alignment indicated by reference of the distal femur may be further adjusted in all six degrees of freedom as a fine tuning for final cut location and orientation. This simply calls for the inclusion of additional adjustment of the location and orientation of the crossbar mechanism 130 and/or rotational alignment arm 140, with respect to the initial reference provide for by contact between the body 150 of the guide 100 and the bone (optionally including the IM Rod 120), in flexion-extension angulation, varus-valgus angulation (rotational angulation and Anterior-Posterior location are already shown), mediolateral location (represented in this embodiment of the current invention by the cross bar mechanism 130 in FIG. 5 where drill guide mediolateral location is shown as being independently and infinitely adjustable), and proximal-distal location (as shown in FIGS. 5, 6, and 7—it should be noted that this adjustment might be best embodied in an infinitely adjustable slide as opposed to the incrementally adjustable slide 160 shown, and that simple marking would be present indicating the relative movement of the slide with respect to the body). It may be desirable to only utilize only a medial drill guide plate 170 with multiple drill guide bushings 180 to create holes extending partially or completely across the femur depending upon the manner in which the guides are to be connected to the femur.

Figure 8:
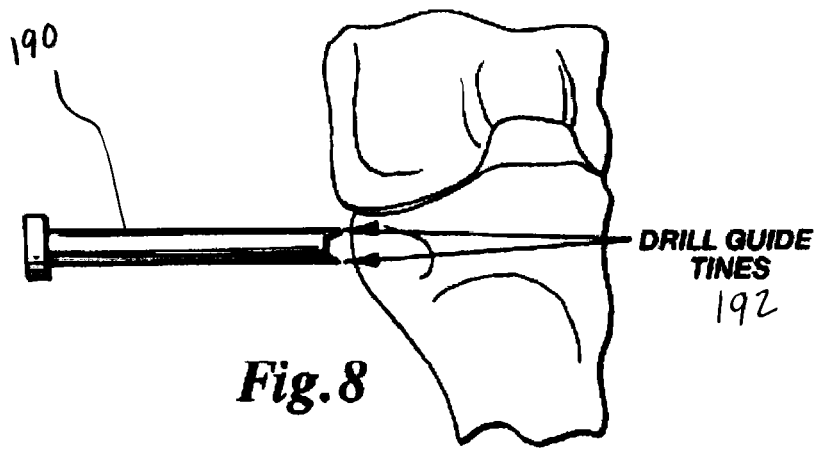
Figure 9:
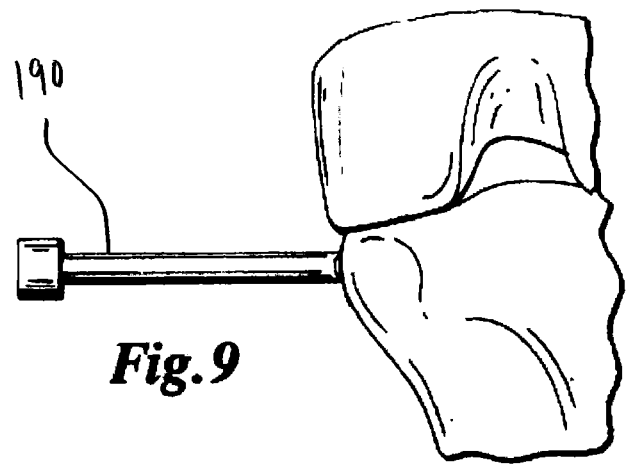
Figure 10:
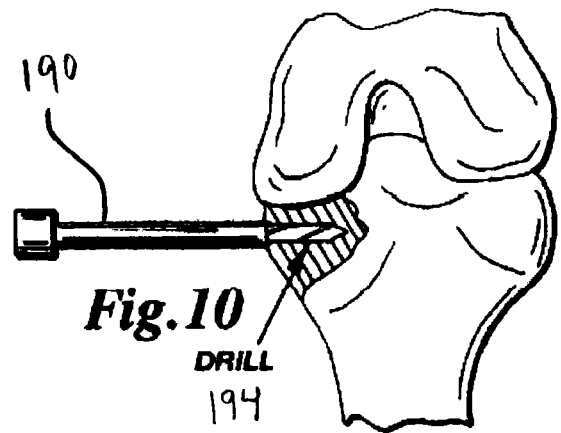
Figure 11:
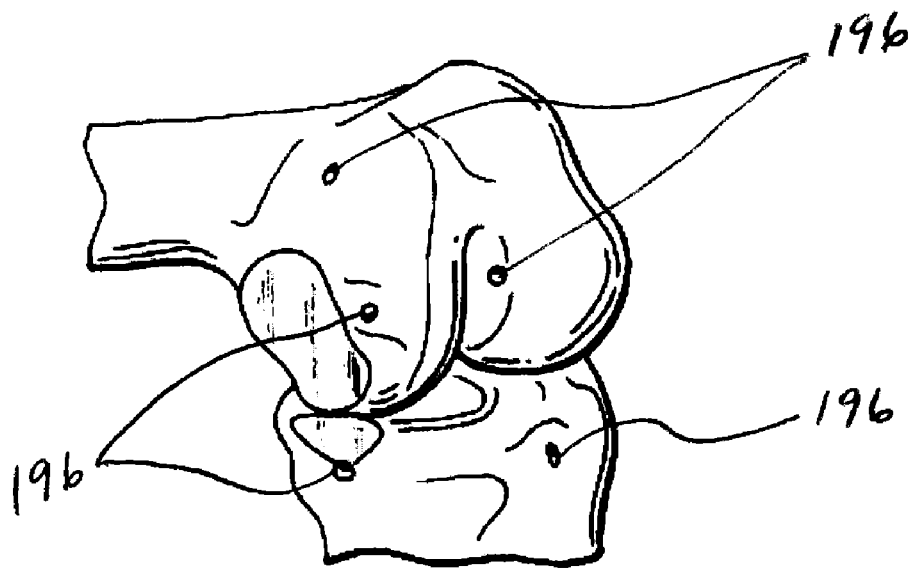

FIGS. 8, 9, and 10 show an alternative alignment/drill guide embodiment of the present invention wherein a cannulated surgically navigated handle/drill guide 190 is used to create fixation apertures in the bone for direct or indirect fixation of a cutting guide. As shown in FIG. 8, it may be advantageous to include tines 192 for penetrating the bone to obtain initial stabilization of the handle in the location and orientation indicated by the surgical navigation system ("Surg Nav"—this term shall be used interchangeably with Computer Aided Surgical System or Image Guided Surgical System throughout this disclosure) prior to extending the drill 194, represented in FIG. 10, into the bone to create the aperture. It should be noted that the aperture 196, or hole, thus created could be blind or extended to a specific depth, or optionally extended entirely through the bone and out the furthest side of the bone. Importantly, this process could be utilized transcutaneously through a small stab wound perhaps 4 mm to 8 mm in length) through the skin to the bone surface, or through a pre-formed incision through which other instrumentation of the present invention, the implant(s), or other devices may be introduced during a procedure. Further, although only one cannulation is shown, a single handle may desirably contain multiple cannulations, some or all of which could be adjustably extended into contact with the bone to reduce any wandering of the drill 194 contacting oblique bone surfaces and improve the precision and accuracy of aperture creation (thus allowing for the creation of apertures 196 in the medial side of the femur, represented in FIG. 11, with a single Surg Nav Handle—Also, the apertures 196 may be configured such that the femoral and tibial apertures 196 shown in FIG. 11 are all created using a single handle with multiple cannulations implemented in a single positioning step for the handle which simultaneously accounts for the location and orientation of the desired cuts on both the femur and tibia). As represented in FIG. 9, there is very little distance over which the drill 194 is cantilevered between its guidance within the cannulation(s) and its point of initial contact with the outer surface of the bone to avoid 'walking' of the drill bit as it contacts oblique bone surfaces. This aspect of this embodiment of the current invention is critical in preserving the potential accuracy of Surg Nav systems, i.e.; the navigation system (the computer and the sensors) may be capable of determining appropriate location and orientation of instrumentation to accuracies within +/−0.5 mm and +/−0.5 degrees, but if the location and/orientation of the aperture(s) created represents some path of least resistance in bone which is followed by the drill 194, the resultant location and orientation of cutting guide, and thereby the cut surfaces, and thereby the location and orientation of the prosthesis attached thereto, will likely be seriously in error. At the end of the day, if the aperture creation step is not carefully controlled, you will have a very expensive alignment system whose stated purpose is to increase reproducibility, and whose method of implementation compromises this stated purpose.

Although not shown, the surgically navigated drill guide benefits from an optional handle feature allowing the surgeon to grasp and manipulate the drill guide, impact the tines into the bone to achieve initial purchase (tapping an impact surface on the end of the handle with a hammer may suffice), and containing a surgical navigation sensor or trackable marker enabling the surgical navigation system to sense and communicate to the surgeon the exact location and orientation of the drill guide in space with respect to the desired aperture location and orientation to be created in the bone or bones.

It should also be noted that the methods described herein are applicable to the methods demonstrated in Provisional Patent Applications No. 60/536,320, entitled "Methods and Apparatus for Pinplasty Bone Resection", and Application No, 60/540,992, entitled "Methods and Apparatus for Wireplasty Bone Resection," the disclosures of each of which are hereby incorporated by reference.

FIGS. 12 Through 34

FIGS. 12-34 disclose embodiments of the present invention for creating planar and/or curvilinear resection surfaces on or in the proximal tibial and other bones and embodiments of the present invention for prosthetic implants.

Figure 40:
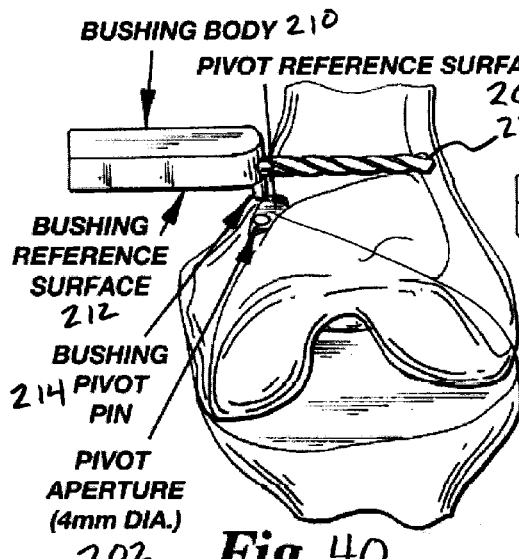
Figure 48:
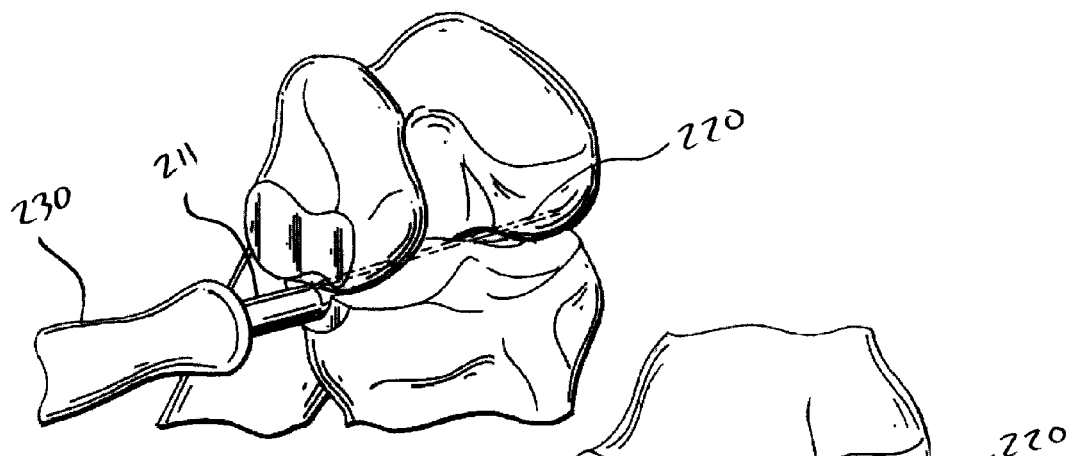
Figure 49:
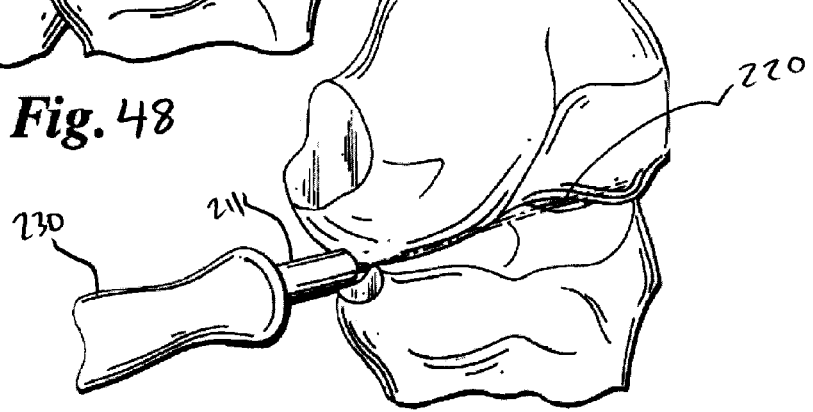
Figure 50:
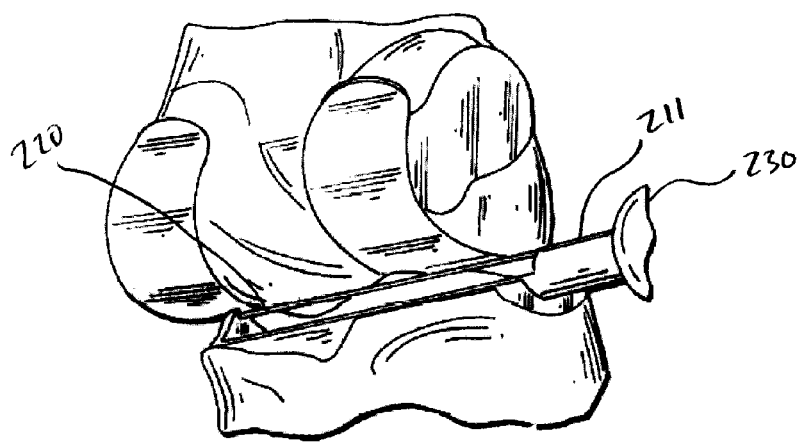

FIGS. 12-15 represents an embodiment of the present invention for cutting guides and cutting tools which substantially comprises a guide 200 with guide pivot aperture(s) 202 and a guide pivot reference surface(s) 204 for mating with a bushing 210 controlling a cutting tool 220, wherein the bushing 210 possess a bushing reference plane 212 (which mates with the pivot reference surface(s) 204 of the guide 200), a bushing pivot pin 214, best represented in FIG. 40 (which mates with the guide pivot aperture(s) 202 of the guide 200), and a cannulation 216 for articulated and/or axial guidance of the cutting tool 220. It should be noted that this and the other embodiments of the present invention may benefit from the addition of a Gripping Handle 230 feature, as shown in FIG. 48. In a preferred embodiment of the present invention, the drive input or spindle 220 extends through the Gripping Handle 230 and the bushing 210.

There are a number of optional features that are highly desirable depending on the preferred method of use utilized for these embodiments of the present invention. The soft tissue protection tip 222 of the cutting tool 220 and the integral soft tissue retractor feature 218 of the bushing body 210 are two principal examples represented in FIG. 20. The soft tissue protection tip 222 can be integrally formed as a part of the cutting tool 220 during its manufacture, be a separate component attached to it, and may, in one preferred embodiment, be free to rotate with respect to the cutting tool 220 (which would be useful in preventing rotating bearing contact between the tip and soft tissue). The integral soft tissue protector 218 is beneficial in preventing or mitigating contact between soft tissue near the area where the cutting tool 220 enters the wound, cuts bone, and exits the wound (in other words, to the right and left of the bushing body 210 shown in FIG. 15). Picturing an incision as being a window into the joint which is somewhat elastically moveable from side to side, the integral soft tissue retractor 218 would act to shift that window to mitigate or prevent contact between the soft tissue (specifically the patella tendon, medial or lateral collateral ligaments, the capsule, skin, fat, etc.) and the cutting surfaces of the cutting tool 220 as the cutting tool 220 is manipulated to cut bone.

Figure 12:
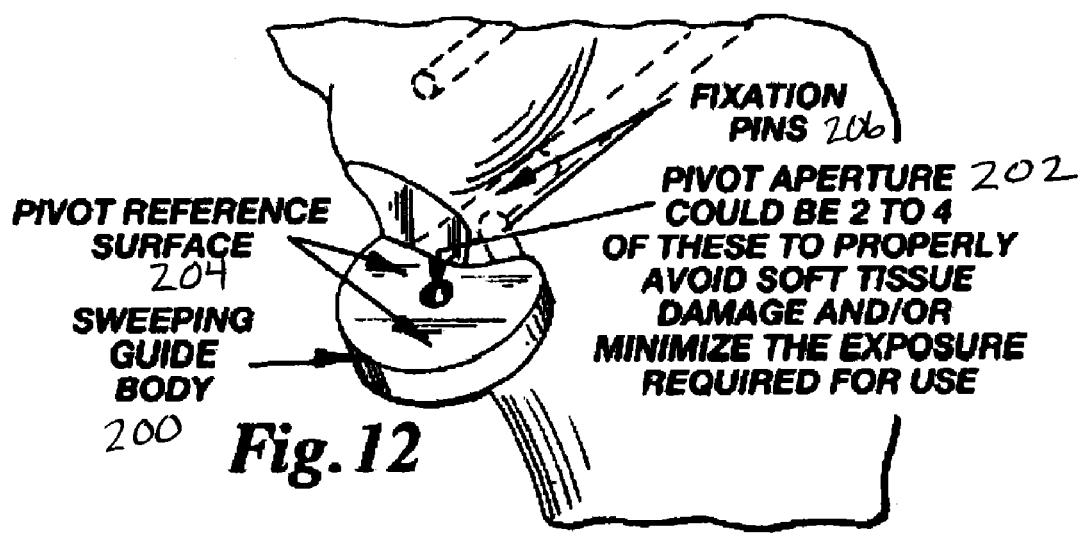
Figure 13:
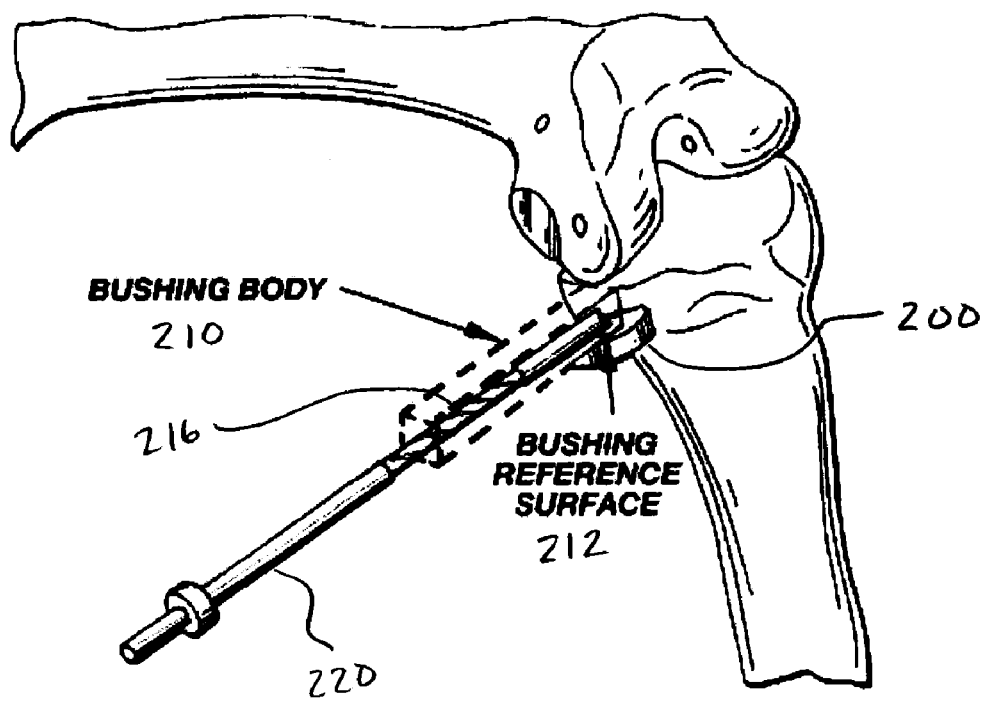
Figure 14:
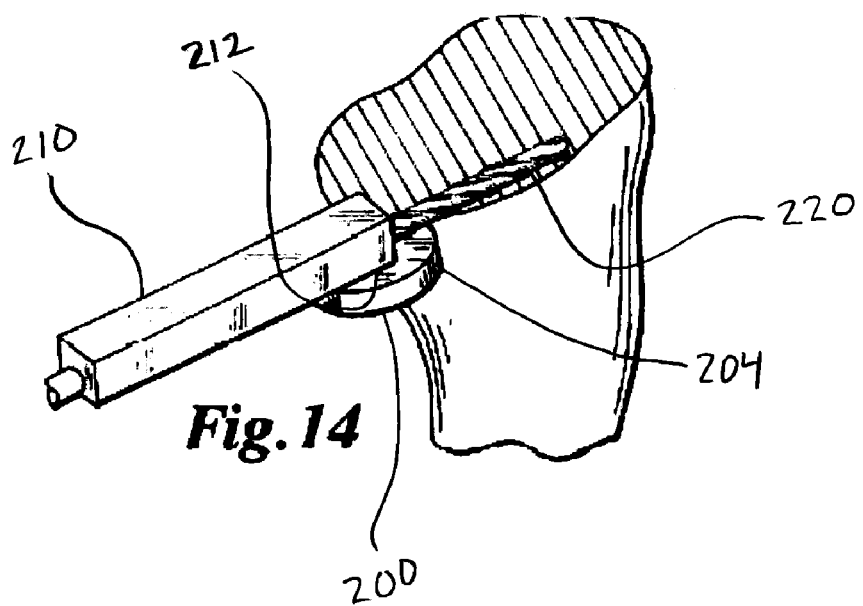

In operation, the guide 200 is properly positioned with respect to the proximal tibia and the cut(s) to be created thereon and robustly fixed with respect to the tibia or directly to the tibia. This can be accomplished by manual alignment means outlined in U.S. Pat. No. 5,643,272 (the '272 patent)

for manually positioning guides then fixing them in place, or use the apparatus and methods described in the '272 patent to create the fixation apertures 196 shown in FIG. 11 or 12, or use the Surgical Navigation techniques known in the art or described herein as shown or in conjunction with the methods described in the '272 patent. The bushing body 210 is then engaged with the guide 200. It should be noted that this form of guide could be accomplished by the addition of a single or multiple guide pivot apertures to the guide of a conventional guide apparatus, such as described in a Surgical Technique published by Johnson & Johnson entitled "P.F.C Sigma RP Knee System."

Figure 15:
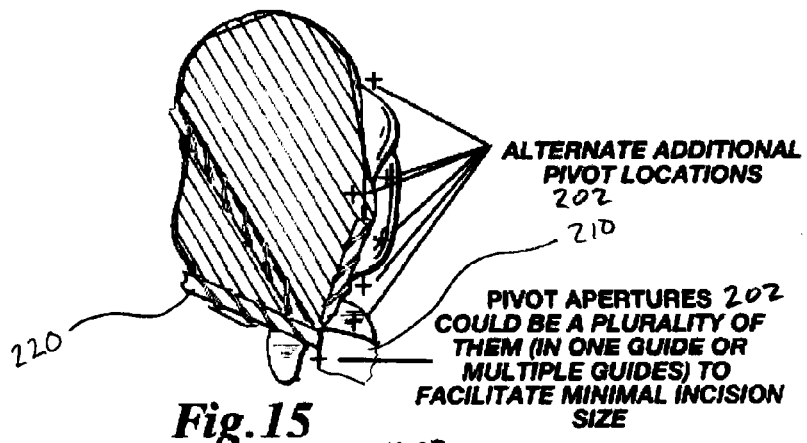
Figure 21:
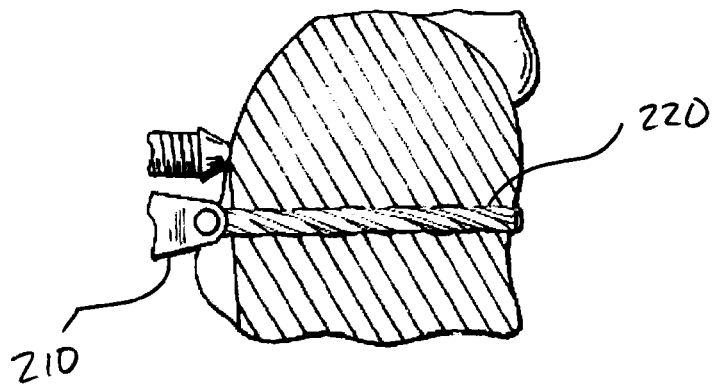
Figure 22:
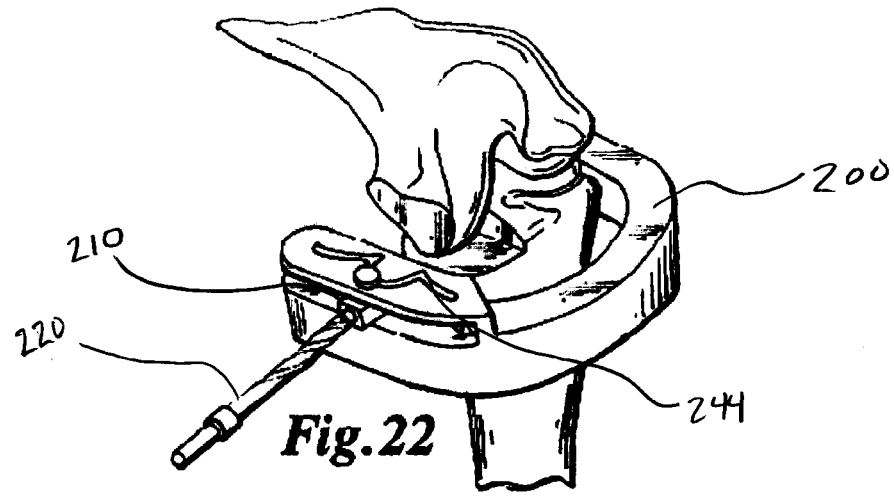
Figure 23:
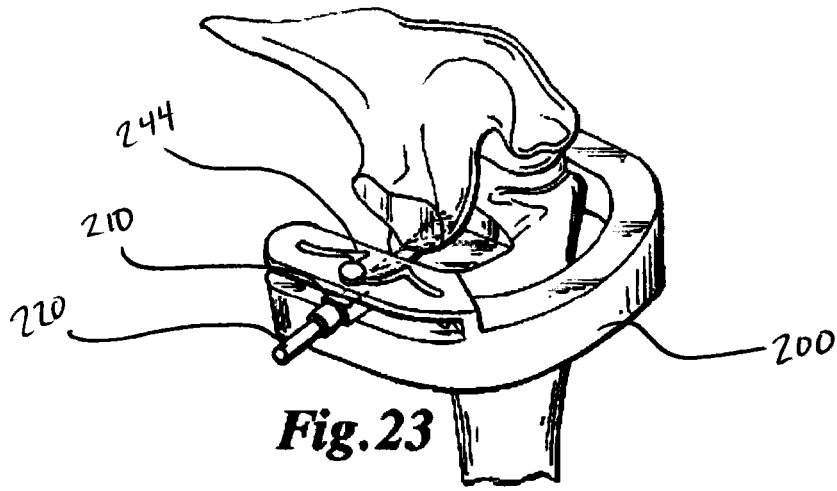
Figure 24:
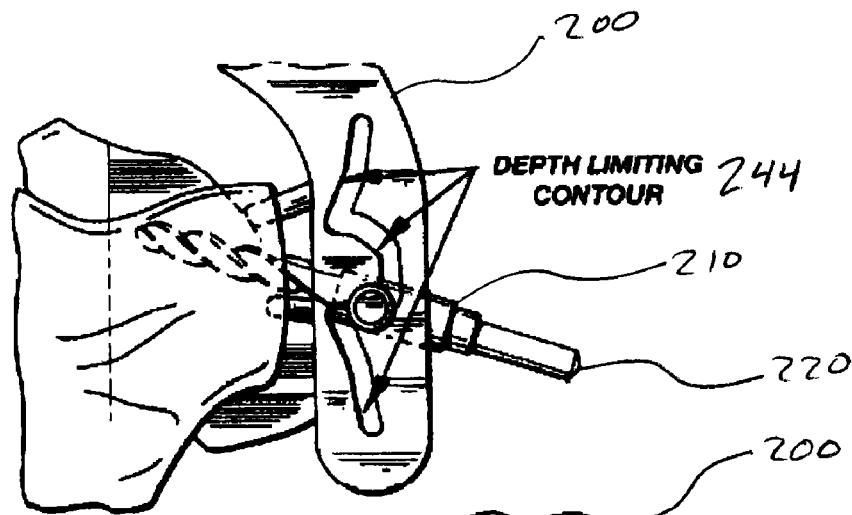
Figure 25:
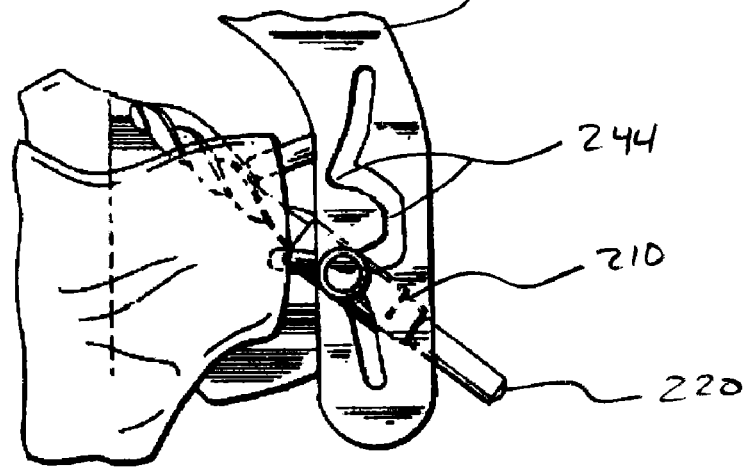
Figure 26:
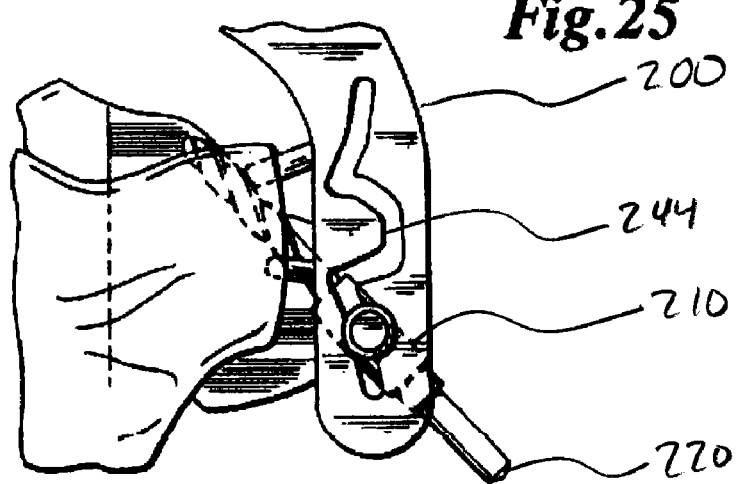

Three primary methods of initiating cutting of the proximal tibia are preferred. The first, or 'Tangent Method', is initiated by extending the side cutting drill through the bushing body cannulation and into contact with a side of the tibia and then sliding the optional non cutting tip along the face of the bone until the cutting surfaces of the cutting tool are first in contact with the side of the bone. At this point, the cutter could be actuated to begin cutting the bony tissue to create the cut surface. As the non-cutting tip cannot cut bone, its edges would remain at all times immediately beyond and adjacent to the boundary of the cut surface being created. The diameter or size may be greater or less than the diameter or size of cutting surfaces of the cutting tool. Note that although the embodiment of the cutting tool shown is a side cutting drill, a modified rat tail rasp driven by a reciprocating driver could also work well—any cutting tool capable of cutting in a direction orthogonal to its long axis is considered to be within the scope of the present invention. As best represented in FIGS. 15 and 21, the entirety of the resected surface may be prepared in this manner. The second primary method is the 'Plunge Then Sweep' method. In this method, the cutting tool or optionally a pilot drill would be plunged completely or partially across the surface to be cut. Then the cutting tool could be swept back and forth in clockwise and counter-clockwise directions while being axially manipulated to complete the cuts. The third primary method is the 'Chop Then Sweep' method represented in comparing FIGS. 40 and 41. In this method, the cutting surfaces of the cutting tool are positioned over and at least partially across the uncut bone, then chopped down into it by manipulating the bushing. In other words, the bushing pivot pin is engaged with the pivot aperture with the cutting tool positioned over the bone which positions the bushing reference surface at a distance above the pivot reference surface, then the bushing is moved downward along the axis of the bushing pivot pin while the cutting tool is under power until the cutting tool reaches the cut surface to be created (if the cutting tool is a side cutting drill, the cutting surfaces would be tangent to the desired cut surface at that time). The bushing is then manipulated as described hereinabove to complete the cuts.

In one embodiment, the pivot reference surface and pivot aperture could be slidably mounted to a base component fixed with respect to the tibia so that the surgeon may manipulate the bushing body to simultaneously create the cut and move the pivot aperture with respect to the tibia. This embodiment will enable the surgeon to easily compensate for any soft tissue condition encountered clinically while preserving the benefits of the present invention. Methods combining the aforementioned primary methods are considered to be within the scope the present invention. Importantly, most standard or prior art tibial resection cutting guides may be modified to include the pivot apertures and pivot surfaces of the guide assembly of this embodiment as described herein.

Figure 16:
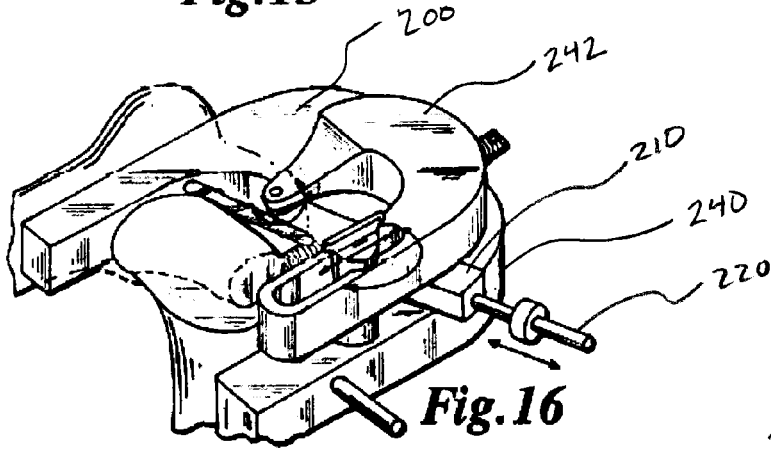
Figure 17:
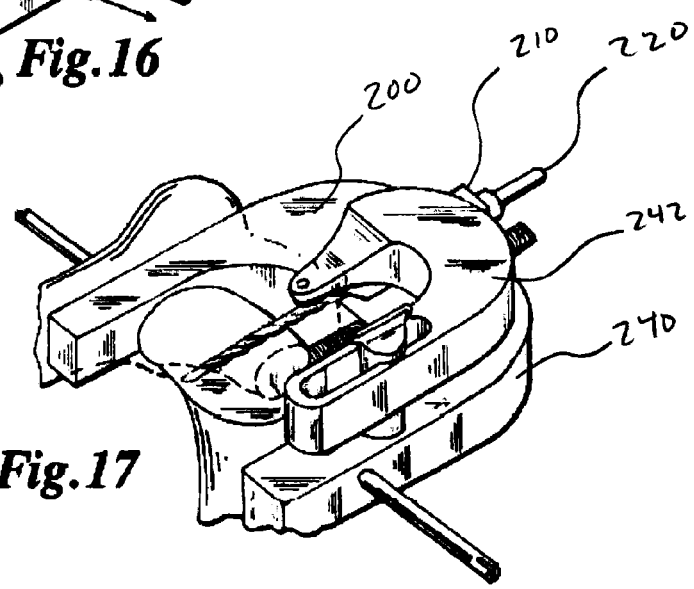

FIGS. 16 through 21 describe another embodiment 200 of the present invention. As shown in FIG. 16, this embodiment includes a Base 240 and a Rotational/Translational Pivot Arm 242 coacting to allow for infinite manipulation of the bushing 210 pivot pin 214 location within a desired plane during the process of removing material from the proximal tibia or other bone. Movement of the Rotational/Translational Pivot Arm 242 in both rotational and translational degrees of freedom within a desired plane allows for any combination of rotational and translational movement of the axis of the bushing pivot pin 214 within its desired plane. In other words, this embodiment of the present invention allows for infinite and continuous adjustability of cutting tool 220 location and orientation with respect to the bone or bones being cut while providing for accurate and precise cut surface creation.

FIGS. 22 through 28 represent another embodiment 200 of the present invention whose principal of operation are similar to previous embodiments, with the exception of including a depth limiting contour 244 which acts as either a definitive limitation for cutting tool 220 depth or as a general guideline for a surgeon to follow as the patient's clinical presentation and the surgeon's judgment dictate. Although the embodiment shown is directed toward Unicondylar tibial preparation, it should be noted that it is highly applicable to Tibial, Patella, and Femoral resection in TKA as well as any other clinical application where such definitive or guideline type depth guidance is desirable.

Figure 30:
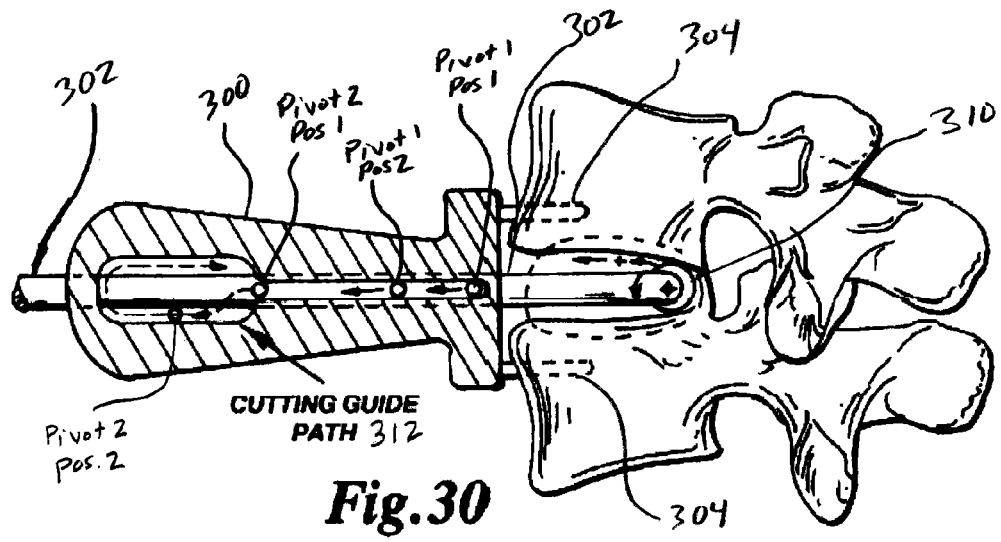

FIGS. 29 and 30 show an embodiment 300 of the present invention directed toward endplate preparation in spinal reconstruction where the endplates are prepared to receive a prosthetic implant. Guide 300 includes a milling handle 302 to which the cutting tool 310 attaches. It is interesting to note that the profile of the cutting path 312 of the guide 300 represented in FIG. 30, in this embodiment, is geometrically identical to the cutting path of the resected surface created by the passage of the cutting tool 310 shown. This could be very helpful in clinical application where such a device where inserted into a wound such that, while the surgeon could not visually observe the cutting tool 310 while it removes bony material, the surgeon could, by way of the guide geometry, observe where the cutting is with respect to the bone being cut by looking at the position (represented by "POS 1" and "POS 2") of 'Pivot 2', represented in FIG. 30, with respect to its location in contact with the guide as it traverses the cutting path of the cutting guide.

This embodiment is also highly applicable to tibial resection and allows for cut geometries that are anatomically curved in both AP and ML profiles to both preserve bone and improve fixation quality and load transfer characteristics between the implant and the bone by converting the shear component load of conventional planar tibial components into compressive loads via geometrically normal or transverse abutment of bone and implant surfaces in the direction of A-P and/or M-L and/or torsional shear loading. An implant design embodying fixation geometries for mating with such cut surfaces is highly desirable. In one embodiment of such a tibial prosthesis design, the fixation surfaces would be intended to mate, directly or indirectly, with cut surfaces represented in FIGS. 33 and/or 34 (the tibia in the right side of the FIG. 34). In essence, the tibial implant would possess a planar or gently curvilinear 'rim' for contacting the 'cortical skim cut' surface (represented in FIG. 32), and convex fixation surfaces for direct or indirect fixation to the concave tibial cuts generally represented in FIGS. 33 and 34. Direct fixation to such surfaces could be achieved by high precision resection of both the cortical rim, for attachment of the rim of the tibial prosthesis, and the concave surface(s), for intimate apposition to the convex implant surfaces. Such fixation, specifically of the concave bone cuts to the convex implant surfaces, could be achieved by way of an interference fit between the cuts and the implant along one axis (for instance, a front to back—AP—axis or direction), or along two axes (for instance, AP and Side to Side—ML—axes), or circumferentially (in other words a bit like a pin of a given diameter being forced into a hole of a lesser diameter), or both circumferentially and along an axis at roughly a 90 degree angle or normal to the skim cut surface when viewed in one or two orthogonal planes (an "up and down axis" or superior-inferior or proximal distal direction). It should be noted that an interference fit in a roughly superior-inferior direction may call for a textured surface on the bottom most surface of the convex fixation surfaces presents a small surface area of contact at initial contact with the bottom of the concave cut to allow the implant to compact a reduced area of cancellous bone as the implant is impacted in a superior to inferior direction until it reaches its desired superior-inferior location and/or contact between the rim of the implant and the skim cut of the cortices. As compared to previous methods of achieving implant fixation, these embodiments of the present invention yield superior stability of implant fixation to bone to an extent reminiscent of the difference between riding a horse wearing a deeply dished saddle and riding a very sweaty horse bareback.

An alternative fixation paradigm allows for less intensive demands for the precision of the fit between concave tibial cuts and convex fixation surface. In essence, the concave surface may be 'excavated' in any desired manner (such as the Cutting Trials shown in FIG. 31 which cut the proximal tibia while the tibia is moved through at least a portion of its range of motion about the femur), and a morselized or granular osteobiological substance, such as tricalcium phosphate, HATCP, or other substances generally described as 'bone substitutes' or autograft or allograft cancellous or cortical bone (in a preferred embodiment, the bone which was removed from the tibia or other patient bone during the creation of the cut(s) is utilized as it is readily available and completely avoids the issues of disease transmission or immune response), is then impacted into the concave surface using a 'form' to create a surface of impact material (referred to herein as the "Impacted Surface") of specific shape and location/orientation with respect to the cortical skim cut and/or the tibia or femur. This form is beneficially shaped in a manner related to the shape of the convex implant fixation surface shape so as to create a specific geometric relationship between the implant fixation surfaces and the Impacted Surface geometry.

It should be noted that the cutting profile of the cutting tool shown in FIG. 29 is curved in manner beneficial to endplate preparation in intervertebral fusion, dynamic disc replacement, and/or nucleus replacement as the cutting profile closely approximately the natural geometry of the endplates and provides for intimate fit with such prostheses' fixation surfaces. In adapting this embodiment to tibial resection in either partial or complete knee replacement, the cutting profile of the tool would be shaped as desired to create the aforementioned cut surfaces in either one continuous movement of a single cutting tool, or incremental use of one or more cutting tools to cut bone to the desired shape and in the appropriate location and orientation, in all degrees of freedom, with respect to the tibia and/or femur and/or patella and/or soft tissues of the knee joint.

Critically, in many applications of the tibial resection embodiments and methods described herein it is desirable that the Superior-Inferior thickness or diameter of the cutting tools used be less than the thickness of the bone to be removed in the creation of the cut surfaces so that the cutting surfaces of the cutting tool not contact soft tissue surface and bone surfaces located above the bone being removed. Alternatively, the cutting tool could be of such a thickness or diameter as to allow for the resection of both the femur and the tibia, or any such contiguous bones, to be prepared simultaneously with the passage of the cutting surfaces of a single tool across or along cut surfaces being created on both bones. Maintaining the desired geometric relationships between the contiguous or adjacent bone ends would be key in this embodiment of the present invention and could easily be obtained and maintained by use of a bracket 304 fixed to the bones to establish and maintain the geometric relationship between said bones (see FIG. 30 for one embodiment of such a bracket 304 employed to establish and maintain alignment between adjacent bones, in this case vertebral bodies.

FIGS. 35-44

FIGS. 35 through 44 represent embodiments of the present invention for femoral resection in TKA that benefit from the apparatus and principles of operation outlined above. As shown in FIGS. 40 through 44, an aperture 202 and a plane 204 are created in bone which actually act as the cutting guide 200 in controlling the location and orientation of the bushing 210 and thereby the cutting tool 220 within a specific plane during the creation of a cut surface. In this embodiment of the present invention, the cannulated drill guide will, in either manual or Surg Nav techniques, be used to guide a forstner style drill bit (the 'guide surface' 200 shown in FIG. 40 could have been created by a modified drill with a leading section 15 mm long by 4 mm in diameter, responsible for the pivot aperture 202, and a 10 mm diameter following section which was about 10 mm long, responsible for the pivot reference surface 204) to create a larger diameter cylindrical aperture the bottom of which would define a pivot reference surface 204 parallel to the cut surface to be created, and a smaller diameter cylindrical aperture to form a pivot aperture 202 for maintaining the body of the bushing 210 shown in FIGS. 40-44 in the proper location and orientation while cutting. Importantly, the technique outlined above is beneficially applied to tibial resection or any other planar or curvilinear resection technique as well.

In one embodiment, the use of internal profile based resection guides allows for single spindle guidance of the side cutting drill or other cutting tool in a very robust manner, while minimizing the trauma to soft tissues necessary to implement these embodiments. Furthermore, the use of these single spindle embodiments lend themselves to easy manipulation of the cutting tool in pivotally sweeping a cut surface while manipulating the cutting tool 220 axially with respect to the bushing 210 (see FIG. 37). Thus the anterior chamfer cut, distal cut, and posterior cut could be completed by sweeping the cutting tool along the cutting path of the cut surface while guided by the cutting guides described in the copending provisional patent applications, and the anterior and/or posterior cuts could be completed by pivotally sweeping the cutting tool 220 as mentioned above, or shown in FIGS. 37 and 40. This is beneficial in that the internally located guide surfaces could be truncated or shortened significantly allowing for both easier insertion into the surgical exposure and reduction in the exposure necessary to accommodate the embodiments in clinical use.

FIGS. 35 through 39 represent apparatus and methods for use in preparing planar or curvilinear cuts. The embodiments of the sweeping guides 200 (perhaps more precisely described as being "pivotally sweeping guides") shown in FIGS. 35 through 39 were previously described in copending applications referenced herein. Stability of fixation of the cutting guides 200 to the bone is critical in this embodiment, as the forces imparted by the surgeon to the bushing 210 must be resisted by the guides 200 lest the resulting cuts vary from their intended location and orientation. One outstanding solution to this issue would be the implementation of a Cam Pin fixation embodiment of the present invention in place of at least one of the fixation nubs 206 shown in FIG. 35. The intent of this cam pin invention would be to 'preload' the fixation of the cutting guide 200 to the bone in a manner that allowed the combination of the bone and cutting guide 200 to act as one continuous structure in resisting deflection of the bushing 210 during bone cutting. This desired end result is attained by having at least one of the fixation nubs 206 being rotatably engaged to the cutting guide 200 such that the axis of the cylindrical surface of the fixation nub 206 contacting the guide 200, and the axis of the cylindrical surface of the fixation nub 206 inserted into the aperture(s) 196 in the bone would not be co-axial or collinear, but would instead be parallel but offset by an distance proportional to the preload desired. This offset embodiment of a fixation nub 206 is herein referred to as a "Cam Pin".

Figure 35:
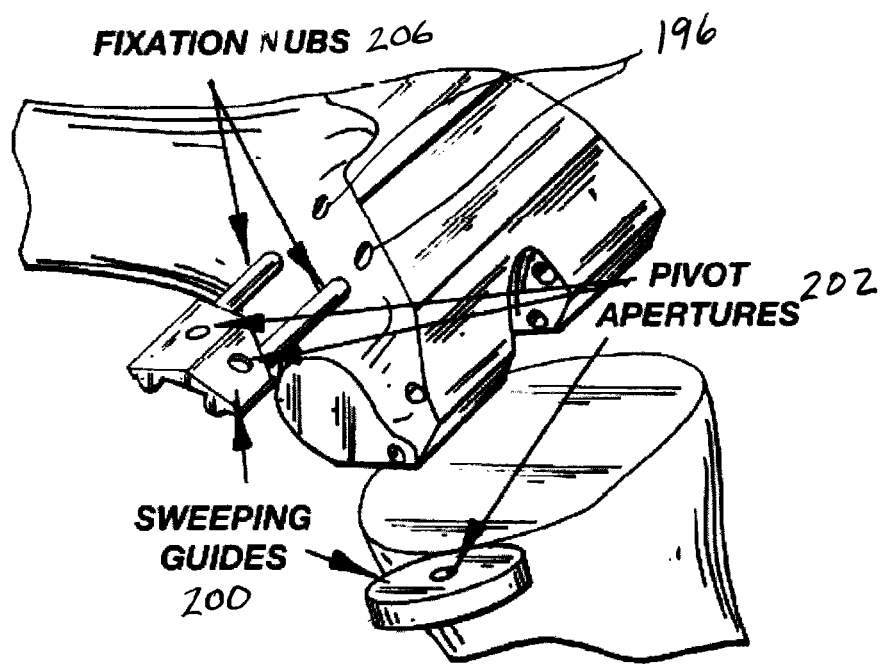
Figure 36:
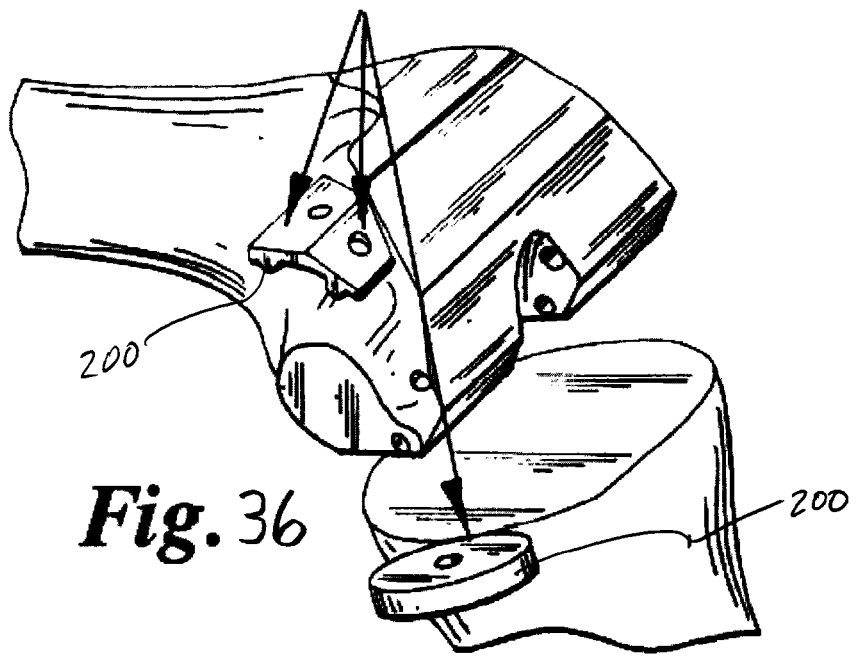
Figure 37:
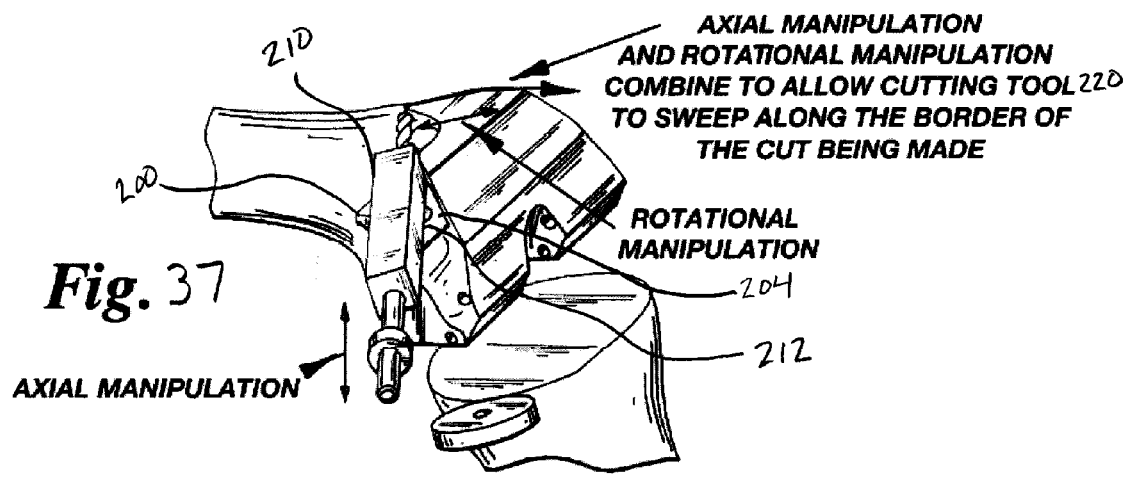
Figure 38:
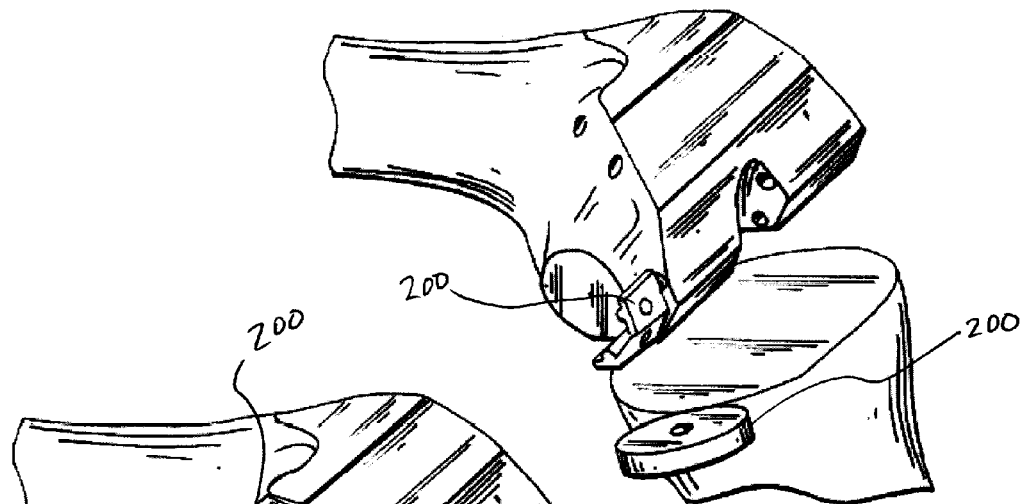
Figure 39:
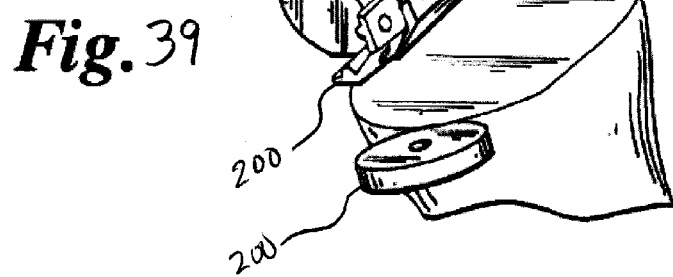

As an example, FIGS. 35 and 36 show the fixation nubs 206 being inserted into two apertures 196 formed in the bone, 0.750 inches apart and 0.158 inches in diameter. In this example, the right most fixation nub 206 shown in FIG. 35 would be integrally formed as part of the cutting guide 200, but the left most fixation nub 206 is a Cam Pin capable of swinging through an arc of 180 degrees (from a "9 O'clock" direction to a "3 O'clock" direction) with an offset between its guide engagement axis and its bone aperture engagement axis of 0.015 inches. With the cam pin oriented at its 9 O'clock direction, the centerline of the integral fixation nub 206 and the bone engagement axis of the Cam Pin would be exactly 0.750 inches to allow for easy insertion of the guide construct 200 into the fixation apertures 196. Once inserted, the guide construct 200 would be robustly fixed to the bone by turning the Cam Pin to the 3 O'clock position creating a nominal interference condition of 0.030 inches simultaneously preloading the guide construct 200 in tension and the bone in compression. As minor deflection or distortion of the guide construct 200 (and the bone, but to a normally much lesser extent) will result, it may be desirable to design the guide such that its desired configuration is this preloaded or deflected or distorted shape and its nominal, unloading condition is designed accordingly. This Cam Pin embodiment of the present invention is applicable under any circumstances where robust fixation between cutting constructs and bone is desired to ensure accurate and/or precise bone cutting. It should be noted that any degree of preload, in tension or compression modes, could be sought and attained through simple modification of the specific example cited above and all such modifications are within the scope of the present invention.

Figure 41:
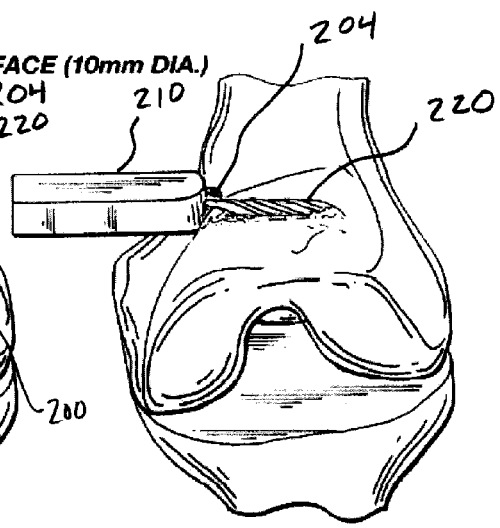
Figure 42:
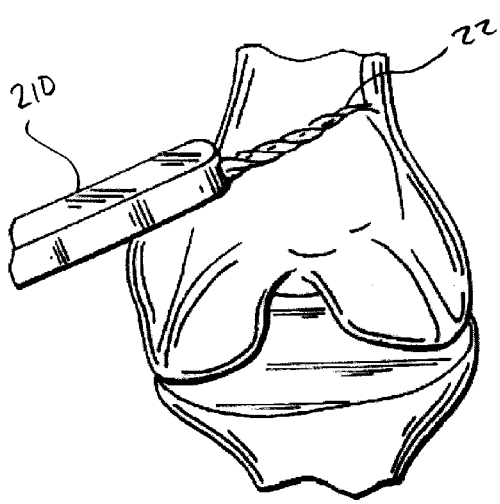
Figure 43:
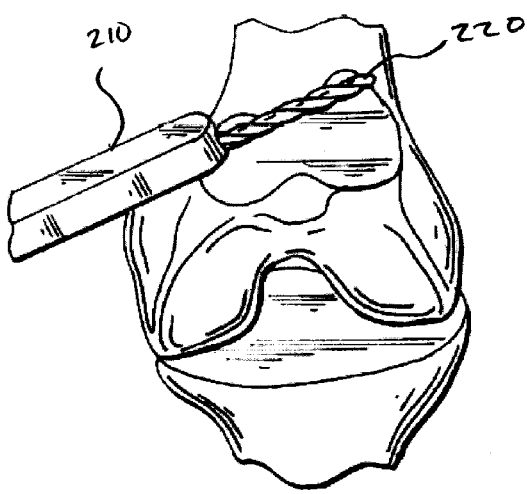
Figure 44:
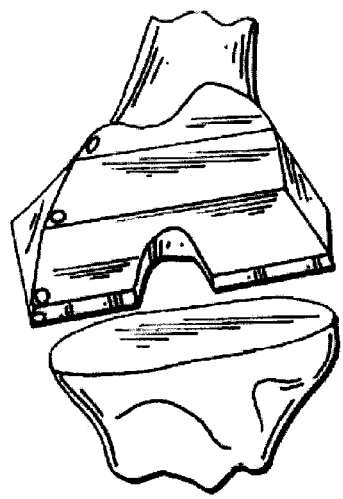

FIGS. 40 through 44 show an embodiment of 'guideless cutting' where properly prepared bone surfaces act as the cutting guide. As shown in FIG. 40 and previously described in the herein reference provisional applications, a modified forstner style drill is used, under manual or surg nav guidance, to create the Pivot Aperture 202 and Pivot Reference Surface 204 in the bone. The bushing body 210 is then engaged to these features as indicated in comparing FIGS. 40 and 41 and manipulated to create the cut(s) for attachment to the implant fixation surface(s) as represented in FIGS. 41 and 42. This method is beneficially applied to the application of tibia resection in creating the tibial cut shown in FIG. 44, as well as any other bone surface resection application.

FIGS. 45 Through 50

Figure 45:
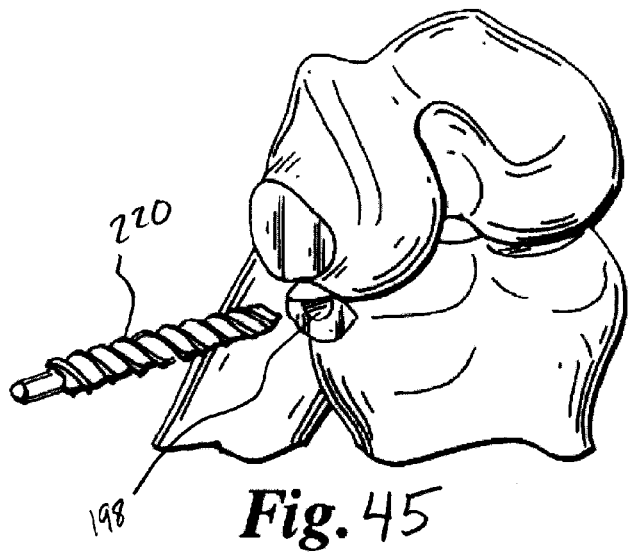
Figure 46:
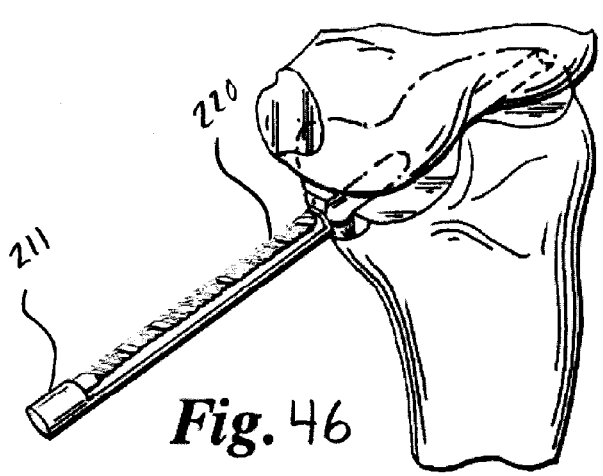

FIGS. 45 through 50 demonstrate implementation of the side cutting drill 220 embodiment of the present invention for cutting tools. It is of interest to note that the modified bushing 211 or "milling handle" shown could further be guided by the PBR guides of the copending provisional patent applications to further combine the accuracy and precision benefits of PBR with the soft tissue protection characteristics of the tibially embedded femoral cutting tool. In utilizing such an embodiment in conjunction with a side cutting drill 220 with a curvilinear cutting profile, it would be critical that the side to side location of the cutting profile of the cutting tool 220 be tightly controlled with respect to the desired side to side location of the implant with respect to the bone as the side to side location of the implant would be dictated by the cut surfaces generated. Alternatively, a cutting tool 220 with a linear cutting profile, as shown in FIG. 46, could be utilized to create cut surfaces with a linear cutting profile and a curved cutting path, and then a second cutter with a curved cutting profile could be used to create a second, contiguous or noncontiguous, cut with a curved cutting profile and/or path whose mediolateral location was closely controlled to result in proper fit and location of the prosthesis attached to said cut surfaces. It should be noted that the cutting path of the second cutter could be located within a single plane, such as for a bilateral femoral component design, or could be curvilinearly divergent from the plane containing the cutting path of the first cut surface. This would be useful for unilateral femoral component designs (ones which require separate left and right femoral implants in TKA) so as to allow for the implant design to reflect out of plane patellofemoral kinematics and/or out of plane tibiofemoral kinematics most accurately.

Interestingly, this embodiment of kinematic resection style resection could be modified to allow the cutting tool to be directly or indirectly linked to the movement of the patella with respect to the femur, or directly connected to the patella, to enable cutting of patellofemoral articular surfaces on the femur while moving the tibia and patella through ranges of motion about the femur. The embodiments of cutting tools for use in attaining this include curvilinear end cutting mills or face cutters, side cutting drills with linear or non-linear cutting profiles, and other cutting tools capable of cutting the femur while engaged, directly or indirectly, to the patella. The side-to-side location of such cutters could be determined by engagement or adjustment with respect to a PBR or other guide, or simply by the natural kinematic path of the patella about the femur during flexion-extension of the knee joint.

In use, the drill 220 (or "Joint Line Drill") shown in FIG. 45 is used to create the aperture 198 formed simultaneously in the femur and the tibia. The drill may be guided by a manually based alignment system to locate a drill guide, or by implementation of the surgically navigated drill guide 190 represented in FIGS. 8 through 11. Although the aperture 198 thus created is shown in these figures as extending in a generally mediolateral orientation, it is important to note that single or multiple apertures of this kind could extend in an anterior-posterior orientation, or an anterior-medial to posteriolateral direction for use in conjunction with surgical exposures that are more anteriorly oriented and/or anteriorly inserted kinematic cutting devices such as the Accuris Uni by Smith & Nephew. Importantly, these embodiments of the present invention allows for partial or complete femoral resection to be performed prior to the initiation and/or completion of the tibial cut surfaces. Upon insertion of the bushing 211 or milling handle shown in FIGS. 46 and 47 into the tibiofemoral aperture, the cutting tool 220 is powered by a rotating, reciprocating, oscillating, radio-frequency based, or ultrasonically based power source, and the tibia is manipulated through a range of motion about the femur to create the cuts best represented in FIG. 50.

Figure 31:
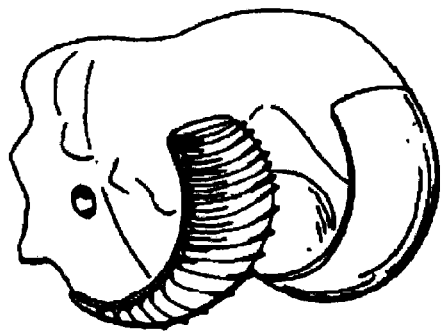
Figure 32:
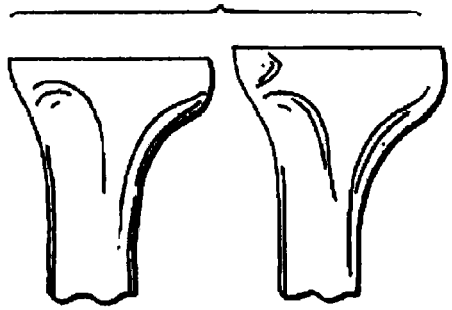
Figure 33:
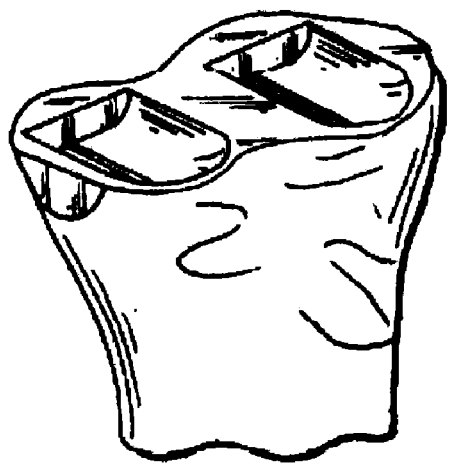
Figure 34:
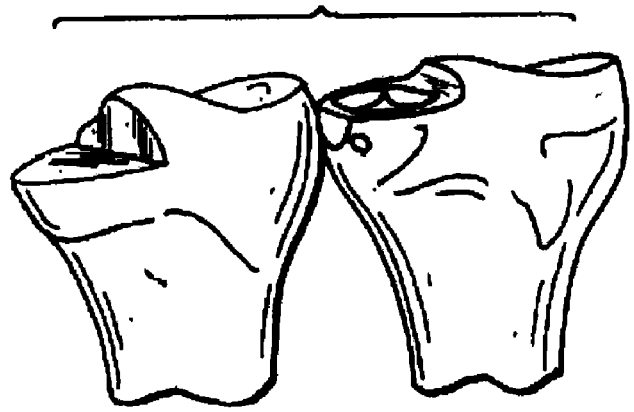
Figure 47:

It is important to note that this embodiment of the present invention, as perhaps best shown in comparing FIGS. 47 and 48, prevents the cutting surfaces of the cutting tool 220 from coming into contact with the soft tissues surrounding the knee joint at any time during the cutting process. The addition of the soft tissue protection sleeves of the copending provisional applications may be desirably added as option to gently displace soft tissue on the medial side of the joint shown in FIG. 48 in the vicinity of the soft tissue portal providing access to the tibiofemoral aperture. It is also of interest to note that this embodiment of the present invention allows for outstanding accuracy and precision in preparing the distal femur to receive a deep range of motion duocondylar prosthesis (essentially two Unicondylar implants interconnected with a modular or integrally formed bridge interconnecting the condylar components), or two separate Unicondylar femoral prostheses (such as represented in FIG. 31, ignoring the cutting feature of the component on the left hand side). It is also important to note that the side cutting drill 220 shown in FIG. 47 may desirable possess a slot cutting feature such as is described in U.S. Pat. No. 5,810,827, where the slot created accommodates a fin feature of the prosthetic femoral component(s) to facilitate robust intraoperative fixation by way of mechanical fit, and long term fixation stability by way of natural biological response to the implant configuration.

Figure 18:
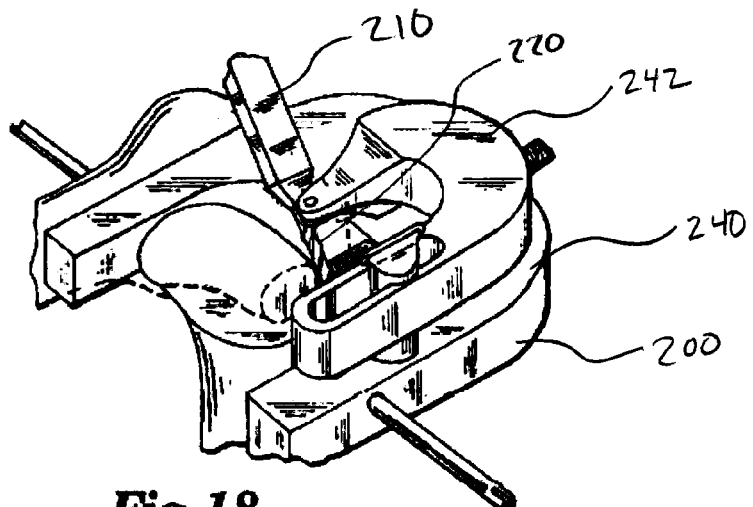
Figure 19:
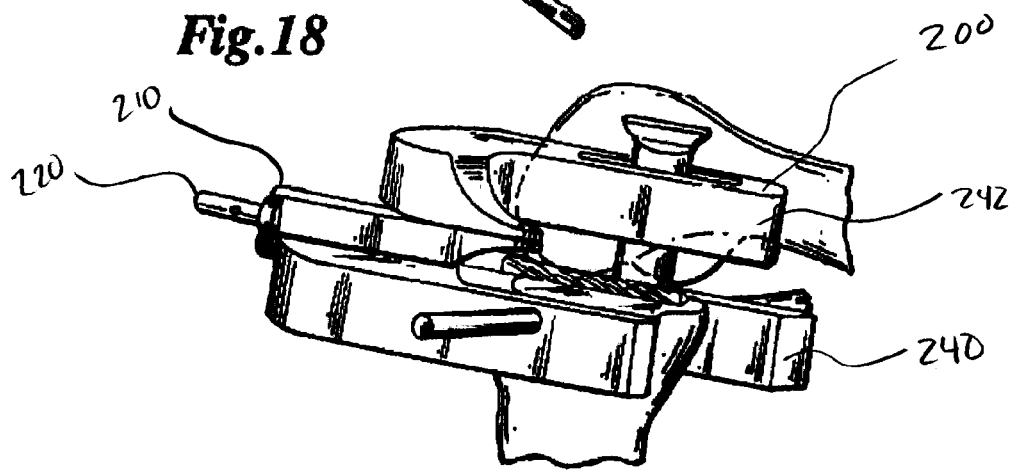
Figure 20:
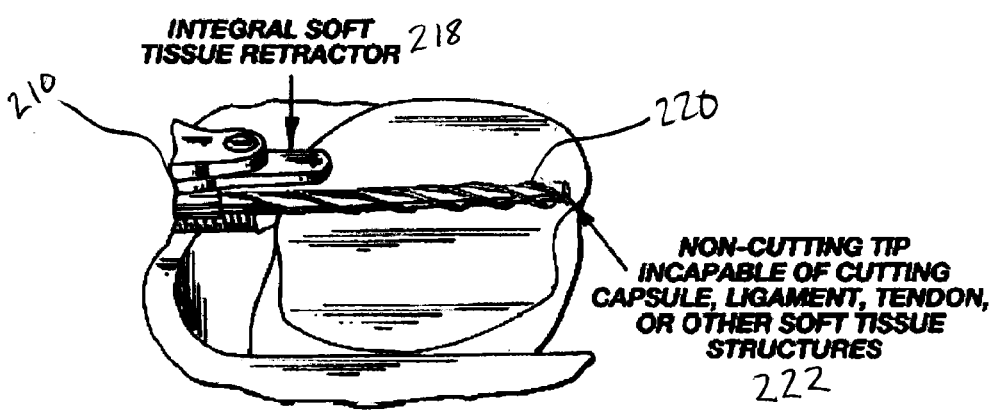

A desirable option for use with this embodiment of the present invention is a continuous distraction device allowing for the location and orientation of the tibia with respect to the femur (and thereby the location and orientation of the tibially embedded cutting tool with respect to the femur) to be reproducibly controlled as the tibia is manipulated through a range of motion about the femur, thus yielding cut surfaces of the desired shape, location, and orientation. One example of such a continuous distraction device is shown in FIG. 18 of U.S. Pat. No. 6,695,848. A very interesting embodiment of the present invention is to improve upon the invention of the '848 patent by positioning such trialing surfaces between the posterior and distal condylar areas and providing engagement features for coacting with the bushing or milling handle to facilitate either or both Trial Reduction Prior to Femoral Resection and Guided Kinematic resection. Determination of the location and orientation of such a continuous distraction embodiment could be determined by manual alignment means or simply a surgical navigation sensor interconnected with a pair of pliers whose sides possessed robust fixation or gripping features adjacent a face or surface(s) shaped to mimic the femoral component articular geometry selected for that knee (i.e.; be radially concentric with respect to the desired implant's condylar articular profile in a ML view). A bushing handle for use in conjunction with such a device may possess engagement features or surfaces for engaging the engagement features of the continuous distraction device. It should also be clear that the embodiments of the present invention could easily be modified to allow for preparation of only one condyle in a conventional Unicondylar surgical procedure wherein the Joint Line Drill and the cutting tool used to create the cut surfaces are extended only across a single compartment of the knee joint.

An alternative to the continuous distraction devices described above would be manual distraction of the single compartment of the knee joint during manipulation of the tibia through a range of motion about the femur during kinematic resection which will be very advantageous in Unicondylar Knee procedures. This method, when applied to medial compartment Unicondylar replacement, involves the surgeon performing at least preliminary soft tissue release in the affected compartment, creating the aperture using the joint line drill while applying a force or moment to or about the joint so as to appropriate tense the ligaments and achieve the desired displacement of the tibia from the femur at that point in the range of motion of the joint and thereby the tibiofemoral aperture would be properly located with respect to both the femur and the tibia. Next the bushing or milling handle would be inserted into the aperture, and, while maintaining the desired tension on the soft tissues via the aforementioned force or moment, sweeping the tibia about the femur while cutting the femur. A skilled surgeon could effectively and consistently implement this technique without the hereinabove mentioned continuous distraction device.

Another feature of the embodiments of the present invention represented in FIGS. 45 through 50 is the preservation of the "island" or "bridge" 197 of bone located between the exposed cutting surfaces of the cutting tool 220 shown in FIG. 47. As the Anterior Cruciate Ligament and the Posterior Cruciate Ligament essentially 'crisscross' each other above this bridge, this embodiment of the present invention guarantees that these ligaments cannot come into contact with the cutting surfaces of the cutting tool, and may, if desired, allow for both condyles to be replaced by the prostheses without negatively impacting the competency of either Cruciate ligament. The ability of these embodiments of the present invention to allow for highly reproducible bone cuts (and implant fit thereto) while simultaneously accounting for proper soft tissue balancing throughout the range of motion of the implanted prostheses while protecting the soft tissues from inadvertent damage by bone cutting tools, while optionally preserving living bone tissue for subsequent revision is a key objective of the present invention.

The complete disclosures of the patents, patent applications and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed:

1. An apparatus configured to guide a cutting tool to create a resected surface in a bone during an arthroplasty procedure, the apparatus comprising:
   a sweeping guide body having fixation features adapted to operably secure the sweeping guide body relative to the bone, the sweeping guide body have a guide pivot reference surface that includes at least one guide pivot aperture defined therein; and
   a bushing assembly having a bushing reference plane, a bushing pivot pin and an axial guide structure with an axial guide lumen defined therein with a long axis corresponding to a long axis of a cutting tool,
   such that, when the fixation features are operably secured to the bone and the bushing assembly operably coacts with the sweeping guide body whereby the bushing reference plane operably mates with the guide pivot reference surface and the bushing pivot pin operably engages with one of the at least one guide pivot apertures, the apparatus is configured to provide articulated and axial guidance of the cutting tool as the cutting tool creates at least a portion of the resected surface by inserting the cutting tool into and beyond the axial guide lumen of the guide structure along a long axis of the bushing assembly and sweeping the cutting tool across at least a portion of the resected surface by pivoting the bushing assembly relative to the sweeping guide body on an axis defined by the bushing pivot pin engaged with the one of the at least one guide pivot apertures, and wherein the bushing assembly further comprises a soft tissue retractor adapted to mitigate contact between the cutting tool and soft tissue surrounding an incision through which the cutting tool is inserted to create the resected surface.

2. The apparatus of claim 1 wherein the guide lumen has an internal cross-section along the long axis of the guide lumen generally corresponding to a cross section of the cutting tool along the long axis of the cutting tool and the guide lumen is adapted to accept cutting tools from the set consisting of: a sagital saw and an ultrasonic blade.

3. The apparatus of claim 1, wherein the guide lumen has an internal cross-section along the long axis of the guide lumen generally corresponding to a cross section of the cutting tool along the long axis of the cutting tool and the guide lumen is adapted to accept a cutting tool comprising a milling bit.

4. The apparatus of claim 1, further comprising a second sweeping guide body having fixation features adapted to operably secure the second sweeping guide body relative to a bone and at least one guide pivot reference surface and guide pivot aperture utilized to provide articulated and axial guidance of the cutting tool as the cutting tool creates at least a portion of the resected surface.

5. The apparatus of claim 1, wherein the aperture in the sweeping guide body comprises an elongate slot.

6. The apparatus of claim 5, wherein the slot includes a depth limiting contour adapted to limit axial movement of the bushing to limit a depth that the cutting tool can cut into the bone.

7. An apparatus configured to guide a cutting tool to create a resected surface in a bone during an arthroplasty procedure, the apparatus comprising:

a sweeping guide body having fixation features adapted to operably secure the sweeping guide body relative to the bone, the sweeping guide body have a guide pivot reference surface that includes at least one guide pivot aperture defined therein; and a bushing assembly having a bushing reference plane, a bushing pivot pin and an axial guide structure with an axial guide lumen defined therein with a long axis corresponding to a long axis of a cutting tool, such that, when the fixation features are operably secured to the bone and the bushing assembly operably coacts with the sweeping guide body whereby the bushing reference plane operably mates with the guide pivot reference surface and the bushing pivot pin operably engages with one of the at least one guide pivot apertures, the apparatus is configured to provide articulated and axial guidance of the cutting tool as the cutting tool creates at least a portion of the resected surface by inserting the cutting tool into and beyond the axial guide lumen of the guide structure along a long axis of the bushing assembly and sweeping the cutting tool across at least a portion of the resected surface by pivoting the bushing assembly relative to the sweeping guide body on an axis defined by the bushing pivot pin engaged with the one of the at least one guide pivot apertures, and wherein the sweeping guide body comprises a base and a pivot arm each having a guide surface that is spaced apart from and facing the other guide surface, the pivot arm connected to and rotationally and translationally adjustable relative to the base.

8. An apparatus configured to guide a cutting tool to create a resected surface in a bone during an arthroplasty procedure, comprising:

a sweeping guide body having fixation features adapted to operably secure the sweeping guide body relative to the bone, the sweeping guide body having a guide pivot reference surface; and a bushing having a bushing reference plane and an axial cannulation adapted to receive a cutting tool, such that, when the fixation features are operably secured to the bone and the bushing operably coacts with the sweeping guide body such that the bushing reference plane operably mates with the guide pivot reference surface, the apparatus is configured to provide articulated and axial guidance of the cutting tool as the cutting tool creates at least a portion of the resected surface by inserting the cutting tool into and beyond the axial cannulation of the bushing and sweeping the cutting tool across at least a portion of the resected surface by pivoting the bushing assembly relative to the sweeping guide body on an axis defined by a pivot point between the bushing and the sweeping guide body, and wherein the bushing includes a soft tissue retractor adapted to mitigate contact between the cutting tool and soft tissue surrounding an incision through which the cutting tool is inserted to create the resected surface.

9. The apparatus of claim 8, wherein the pivot point between the bushing and the sweeping guide body is fixed.

10. The apparatus of claim 9, wherein the pivot point between the bushing and the sweeping guide body is defined by a pin mated with an aperture.

11. The apparatus of claim 10, wherein the pin is defined on the bushing and the aperture is defined in the sweeping guide body.

12. The apparatus of claim 8, wherein the sweeping guide body comprises a base and a pivot arm each having a guide surface that is spaced apart from and facing the other guide surface, the pivot arm connected to and rotationally and translationally adjustable relative to the base.

13. The apparatus of claim 8, wherein the pivot point includes a pin connected to the bushing inserted into an elongate slot in the sweeping guide body.

14. The apparatus of claim 13, wherein the slot includes a depth limiting contour adapted to limit axial movement of the bushing to limit a depth that the cutting tool can cut into the bone.

* * * * *